United States Patent
Locke et al.

(10) Patent No.: US 10,398,604 B2
(45) Date of Patent: Sep. 3, 2019

(54) DRESSING WITH OFFLOADING CAPABILITY

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

(*) Notice: Subject to any disclaimer, the term of this patent is extended or adjusted under 35 U.S.C. 154(b) by 301 days.

(21) Appl. No.: 14/965,675

(22) Filed: Dec. 10, 2015

(65) Prior Publication Data

US 2016/0175156 A1    Jun. 23, 2016

Related U.S. Application Data

(60) Provisional application No. 62/092,991, filed on Dec. 17, 2014.

(51) Int. Cl.
*A61F 13/00* (2006.01)
*A61F 13/02* (2006.01)
*A61M 1/00* (2006.01)

(52) U.S. Cl.
CPC .. *A61F 13/00068* (2013.01); *A61F 13/00029* (2013.01); *A61F 13/00042* (2013.01);
(Continued)

(58) Field of Classification Search
CPC .......... A61F 13/00068; A61F 13/00029; A61F 13/00042; A61F 13/00055; A61F 13/0203;
(Continued)

(56) References Cited

U.S. PATENT DOCUMENTS 1,355,846 A    10/1920    Rannells
1,944,834 A    1/1934    Bennett
(Continued)

FOREIGN PATENT DOCUMENTS

AU    550575 B2    3/1986
AU    745271 B2    3/2002
(Continued)

OTHER PUBLICATIONS

European Search Report for corresponding Application No. 15192606.0 dated Feb. 24, 2016.
(Continued)

*Primary Examiner* — Adam Marcetich
*Assistant Examiner* — Jessica R Arble

(57) ABSTRACT

Illustrative embodiments of a dressing for treating a tissue site may include a fluid transport layer, an offloading layer, and a liquid deflector. The offloading layer may be in fluid communication with the fluid transport layer, and the offloading layer may include a force offloading region and a target region. The liquid deflector may be positioned between the fluid transport layer and the offloading layer. The liquid deflector may be configured to deflect a liquid from the tissue site into contact with the target region of the offloading layer. The target region may be configured to expand for offloading forces at the tissue site. Other dressings, systems, and methods are disclosed.

18 Claims, 10 Drawing Sheets

(52) U.S. Cl.
CPC .... *A61F 13/00055* (2013.01); *A61F 13/0203* (2013.01); *A61F 13/0216* (2013.01); *A61F 13/0223* (2013.01); *A61M 1/0088* (2013.01)

(58) Field of Classification Search
CPC .............. A61F 13/0216; A61F 13/0223; A61F 13/51305; A61M 1/0088
See application file for complete search history.

(56) References Cited

U.S. PATENT DOCUMENTS

| | | |
|---|---|---|
| 2,547,758 A | 4/1951 | Kelling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,183,116 A | 5/1965 | Schaar |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,025,783 A * | 6/1991 | Lamb .................. A61F 13/0203 428/317.1 |
| 5,028,597 A | 7/1991 | Kodama et al. |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |

(56) References Cited

U.S. PATENT DOCUMENTS

| | | |
|---|---|---|
| 5,585,178 A | 12/1996 | Calhoun et al. |
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,877,873 B2 | 1/2018 | Coulthard et al. |
| 9,956,120 B2 | 5/2018 | Locke |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0082897 A1 | 4/2004 | Rangel et al. |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0161937 A1 | 7/2007 | Aali |
| 2007/0185426 A1* | 8/2007 | Ambrosio ............... A61L 27/52 602/43 |
| 2007/0225663 A1 | 9/2007 | Watt et al. |

(56) References Cited

U.S. PATENT DOCUMENTS

| | | |
|---|---|---|
| 2007/0265585 A1 | 11/2007 | Joshi et al. |
| 2007/0265586 A1 | 11/2007 | Joshi et al. |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0272784 A1 | 10/2010 | Kantner |
| 2010/0305490 A1* | 12/2010 | Coulthard ........... A61M 1/0088 602/43 |
| 2010/0305524 A1 | 12/2010 | Vess et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0224631 A1 | 9/2011 | Simmons et al. |
| 2011/0229688 A1 | 9/2011 | Cotton |
| 2011/0230849 A1* | 9/2011 | Coulthard ........... A61M 1/0088 604/319 |
| 2011/0244010 A1 | 10/2011 | Doshi |
| 2011/0257617 A1 | 10/2011 | Franklin |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0040131 A1 | 2/2012 | Speer |
| 2012/0123359 A1 | 5/2012 | Reed |
| 2012/0143157 A1 | 6/2012 | Riesinger |
| 2012/0258271 A1 | 10/2012 | Maughan |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0152945 A1 | 6/2013 | Locke et al. |
| 2014/0039423 A1 | 2/2014 | Riesinger |
| 2014/0039424 A1 | 2/2014 | Locke |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0309574 A1 | 10/2014 | Cotton |
| 2014/0350494 A1* | 11/2014 | Hartwell ............. A61F 13/0216 604/319 |
| 2014/0352073 A1* | 12/2014 | Goenka ................. D06M 23/00 5/691 |
| 2015/0030848 A1 | 1/2015 | Goubard |
| 2015/0057625 A1 | 2/2015 | Coulthard |
| 2015/0080788 A1 | 3/2015 | Blott et al. |
| 2015/0119830 A1 | 4/2015 | Luckemeyer et al. |
| 2015/0119833 A1 | 4/2015 | Coulthard et al. |
| 2015/0141941 A1 | 5/2015 | Allen et al. |
| 2015/0190286 A1 | 7/2015 | Allen et al. |
| 2016/0000610 A1 | 1/2016 | Riesinger |
| 2016/0067107 A1 | 3/2016 | Cotton |
| 2016/0135998 A1* | 5/2016 | Riesinger .......... A61F 13/00068 604/543 |
| 2016/0144084 A1* | 5/2016 | Collinson ............... A61L 15/42 604/319 |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| DE | 202014100383 U1 | 2/2015 |
| EP | 0097517 A1 | 1/1984 |
| EP | 0100148 A1 | 2/1984 |
| EP | 0117632 A2 | 9/1984 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | S62139523 U | 9/1987 |
| JP | 2005205120 A | 8/2005 |
| JP | 2007254515 A | 10/2007 |
| JP | 2008080137 A | 4/2008 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01/36188 A1 | 5/2001 |
| WO | 01/60296 A1 | 8/2001 |
| WO | 0168021 A1 | 9/2001 |
| WO | 0185248 A1 | 11/2001 |
| WO | 0190465 A2 | 11/2001 |
| WO | 0243743 A1 | 6/2002 |
| WO | 02062403 A1 | 8/2002 |

(56) References Cited

FOREIGN PATENT DOCUMENTS

| WO | 03-018098 | A2 | 3/2003 |
|---|---|---|---|
| WO | 03045294 | A1 | 6/2003 |
| WO | 03045492 | A1 | 6/2003 |
| WO | 03053484 | A1 | 7/2003 |
| WO | 2004024197 | A1 | 3/2004 |
| WO | 2004037334 | A1 | 5/2004 |
| WO | 2004112852 | A1 | 12/2004 |
| WO | 2005002483 | A2 | 1/2005 |
| WO | 2005062896 | A2 | 7/2005 |
| WO | 2005105176 | A1 | 11/2005 |
| WO | 2005123170 | A1 | 12/2005 |
| WO | 2007022097 | A2 | 2/2007 |
| WO | 2007030601 | A2 | 3/2007 |
| WO | 2007070269 | A1 | 6/2007 |
| WO | 2007085396 | A1 | 8/2007 |
| WO | 2007087811 | A1 | 8/2007 |
| WO | 2007113597 | A2 | 10/2007 |
| WO | 2007133618 | A2 | 11/2007 |
| WO | 2008026117 | A1 | 3/2008 |
| WO | 2008041926 | A1 | 4/2008 |
| WO | 2008048527 | A2 | 4/2008 |
| WO | 2008054113 | A1 | 5/2008 |
| WO | 2008/082444 | A2 | 7/2008 |
| WO | 2008/100440 | A1 | 8/2008 |
| WO | 2008104609 | A1 | 9/2008 |
| WO | 2008/131895 | A1 | 11/2008 |
| WO | 2009/002260 | A1 | 12/2008 |
| WO | 2008149107 | A1 | 12/2008 |
| WO | 2009066105 | A1 | 5/2009 |
| WO | 2009066106 | A1 | 5/2009 |
| WO | 2009081134 | A1 | 7/2009 |
| WO | 2009089016 | A1 | 7/2009 |
| WO | 2009/124100 | A1 | 10/2009 |
| WO | 2009126103 | A1 | 10/2009 |
| WO | 2010016791 | A1 | 2/2010 |
| WO | 2010032728 | A1 | 3/2010 |
| WO | 2010/056977 | A2 | 5/2010 |
| WO | 2010129299 | A2 | 11/2010 |
| WO | 2011008497 | A2 | 1/2011 |
| WO | 2011/049562 | A1 | 4/2011 |
| WO | 2011043786 | A1 | 4/2011 |
| WO | 2011115908 | A1 | 9/2011 |
| WO | 2011121127 | A1 | 10/2011 |
| WO | 2011130570 | A1 | 10/2011 |
| WO | 2011162862 | A1 | 12/2011 |
| WO | 2012/112204 | A1 | 8/2012 |
| WO | 2012104584 | A1 | 8/2012 |
| WO | 2012140378 | A1 | 10/2012 |
| WO | 2012143665 | A1 | 10/2012 |
| WO | 2013009239 | A1 | 1/2013 |
| WO | 2013090810 | A1 | 6/2013 |
| WO | 2014022400 | A1 | 2/2014 |
| WO | 2014039557 | A1 | 3/2014 |
| WO | 2014078518 | A1 | 5/2014 |
| WO | 2014/113253 | A1 | 7/2014 |
| WO | 2014140608 | A1 | 9/2014 |
| WO | 2014143488 | A1 | 9/2014 |
| WO | 2015/065615 | A1 | 5/2015 |
| WO | 2015130471 | A1 | 9/2015 |
| WO | 2017048866 | A1 | 3/2017 |

OTHER PUBLICATIONS

International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for PCT/GB2008/004216 dated Jul. 2, 2009.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Non-Final Office Action dated Jul. 20, 2011 for U.S. Appl. No. 12/398,904.
V.A. Solovev et al., Guidelines, The Method of Treatment of Immagure External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatement of Open Septic Wounds," in All-Union Conference on Wounds and Wound Infections: Presentation Abstracts, edited by B.M. Kostyuchenok et al. (Mosco, U.S.S.R. Oct. 28-29, 1986) pp. 91-92 ("Bagautdinov II").
V.A. Solovev, Dissertation Abstract, Treatement and Prevention of Suture Failures after Gastric Resection (S.M. Kirov Gorky State Medical Institute, Gorky, U.S.S.R. 1998 ("Solovev Abstract").
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
International Search Report and Written Opinion for corresponding PCT application PCT/US2016/051768 dated Dec. 15, 2016.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).

(56) References Cited

OTHER PUBLICATIONS

European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
EP Examination Report for corresponding application 12705381.7, dated May 22, 2014.
NPD 1000 Negative Pressure Would Therapy System, Kalypto Medical, pp. 1-4, dated Sep. 2008.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
Louis C. Argenta, MD and Michael J. Morykwas, PhD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G Zivadinovic, V Dukic, Z Maksimovic, D Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Office Action for related U.S. Appl. No. 13/982,650, dated Dec. 14, 2017.
Australian Office Action for related application 2013344686, dated Nov. 28, 2017.

(56) References Cited

OTHER PUBLICATIONS

Office Action for related U.S. Appl. No. 14/517,521, dated Dec. 12, 2017.
Office Action for related U.S. Appl. No. 14/490,898, dated Jan. 4, 2018.
International Search Report and Written Opinion for related appplication PCT/US2017/058209, dated Jan. 10, 2018.
International Search Report and Written Opinion for related application PCT/US2016/047351, dated Nov. 2, 2016.
Office Action for related U.S. Appl. No. 14/919,055, dated Jan. 23, 2018.
Egnell Minor: Addition to the Users Manual Concerning Overflow Protection—Concerns all Egnell Pumps, Feb. 3, 1983, pp. 2.
Extended European Search Report for related application 17177013.4, dated Mar. 19, 2018.
Extended European Search Report for related application 16793298.7, dated Mar. 27, 2018.
Office Action for related U.S. Appl. No. 15/307,472, dated Oct. 18, 2018.
Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 14/080,348, dated Apr. 12, 2019.
Office Action for related U.S. Appl. No. 15/410,991, dated May 2, 2019.

* cited by examiner

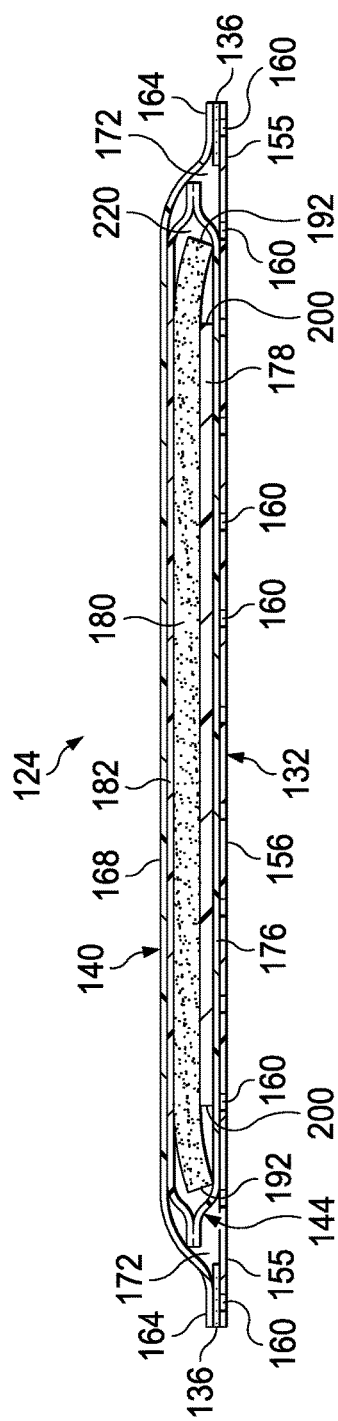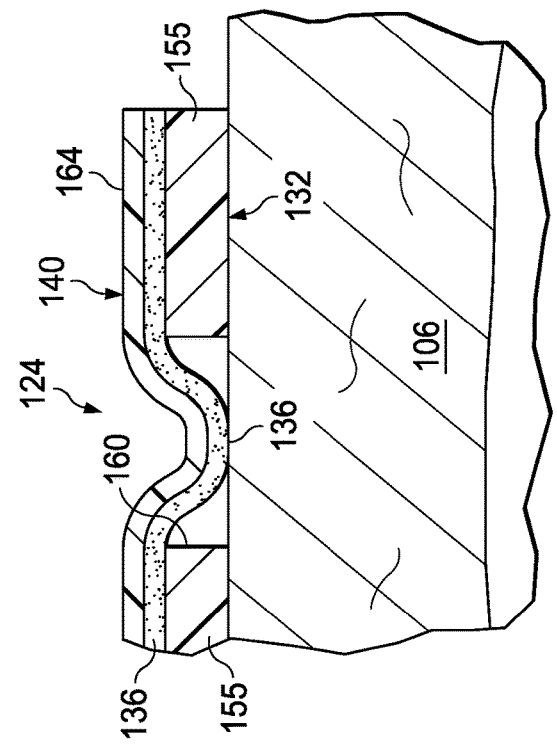

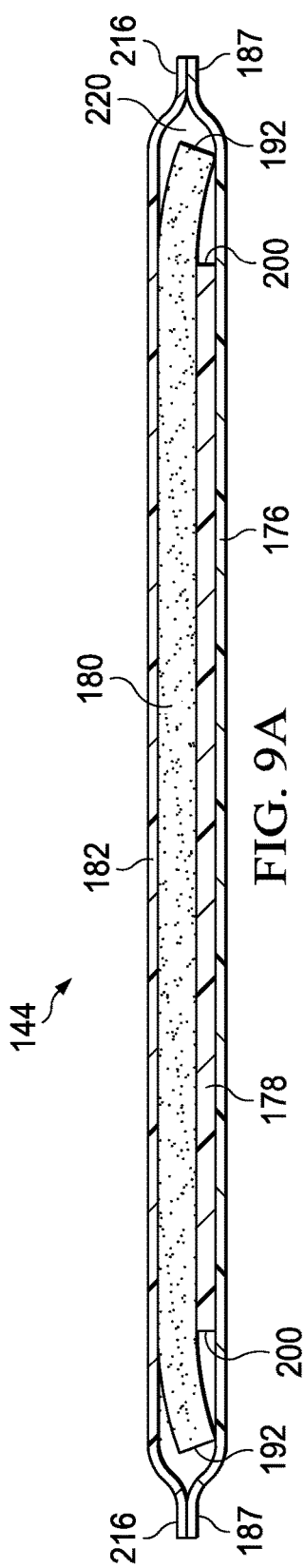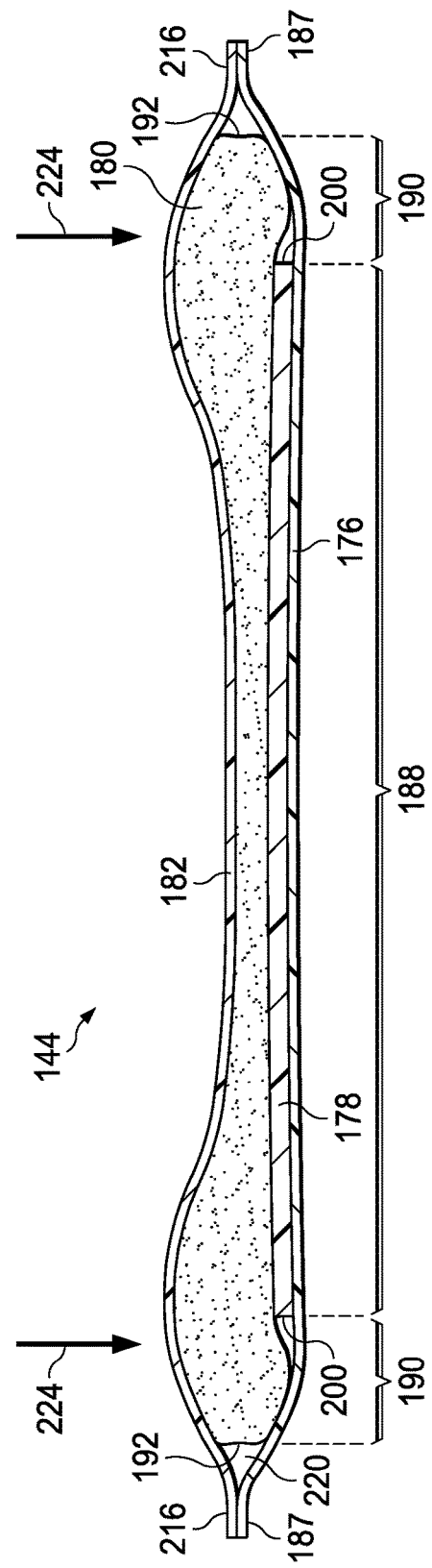

__US 10,398,604 B2__

DRESSING WITH OFFLOADING CAPABILITY

RELATED APPLICATION

This application claims the benefit, under 35 USC 119(e), of the filing of U.S. Provisional Patent Application No. 62/092,991, entitled "Dressing with Offloading Capability," filed Dec. 17, 2014, which is incorporated herein by reference for all purposes.

FIELD

This disclosure relates generally to medical treatment systems and, more particularly, but not by way of limitation, to absorbent dressings, systems, and methods for treating a tissue site with or without application of reduced pressure.

BACKGROUND

Medical dressings may provide for the management of fluid at a tissue site in a variety of ways. Such dressings may be configured to retain or absorb fluid from a tissue site when used with or without reduced pressure. However, the application of reduced pressure to a dressing and a tissue site may enhance the treatment of the tissue site in some instances. In general, reduced pressure may be used for, among other things, reduced-pressure therapy to encourage granulation at a tissue site, draining fluids at a tissue site, closing a wound, reducing edema, promoting perfusion, and fluid management.

Challenges may exist, for example, from swelling in a dressing that may occur when the dressing retains or absorbs fluid while treating a tissue site. Such swelling may cause discomfort and interfere with healing. Further, some tissue sites may be difficult to reach or otherwise have limited access for the application of a dressing, which may present additional challenges. Thus, a need exists for improvements to dressings, systems, and methods that can enhance the management of fluid at a tissue site.

SUMMARY

In some illustrative embodiments, a dressing for treating a tissue site may include a fluid transport layer, an offloading layer, and a liquid deflector. The fluid transport layer may include a first side and a second side configured to be in fluid communication with the tissue site. The first side of the fluid transport layer may be adapted to be positioned facing the tissue site. The offloading layer may be in fluid communication with the fluid transport layer. The offloading layer may include a force offloading region and a target region. The liquid deflector may be positioned between the second side of the fluid transport layer and the offloading layer. The liquid deflector may be configured to deflect a liquid from the tissue site into contact with the target region of the offloading layer.

In some illustrative embodiments, a system for treating a tissue site may include a dressing and a reduce-pressure source. The dressing may include a base layer, a sealing member, a fluid transport layer, an enclosing layer, an offloading layer, and a liquid deflector. The base layer may include a periphery and a central portion. A plurality of apertures may be disposed through the base layer. The sealing member may include a periphery and a central portion. The periphery of the sealing member may be positioned proximate to the periphery of the base layer. The fluid transport layer may be positioned between the base layer and the sealing member. The enclosing layer may be positioned between the fluid transport layer and the sealing member. The offloading layer may be positioned between the fluid transport layer and the enclosing layer, and the offloading layer may comprise a force offloading region and a target region. The liquid deflector may be positioned between the fluid transport layer and the offloading layer. The liquid deflector may be configured to deflect a liquid toward the target region of the offloading layer. The reduced-pressure source may be adapted to be in fluid communication with the dressing to provide reduced pressure to the tissue site.

In some illustrative embodiments, a method of offloading a force at a tissue site may include positioning an offloading layer at the tissue site. The offloading layer may comprise a force offloading region and a target region, and the target region may be positioned at a periphery of the tissue site. Further, the method may include expanding at least the target region of the offloading layer such that the target region is expanded more than the force offloading region.

Other aspects, features, and advantages of the illustrative embodiments will become apparent with reference to the drawings and detailed description that follow.

BRIEF DESCRIPTION OF THE DRAWINGS

FIG. 2 is a cut-away view of the dressing of FIG. 1 shown without a conduit interface;

FIG. 3 is detail view taken at reference FIG. 3, depicted in FIG. 1, illustrating the dressing of FIG. 1 positioned proximate to tissue around the tissue site;

FIG. 9A is a cut-away view of the fluid management assembly of FIG. 6, depicting the fluid management assembly in a dry or unsaturated state prior to use;

FIG. 9B is a cut-away view of the fluid management assembly of FIG. 6, depicting the fluid management assembly in a fluid saturated state during or after use;

DETAILED DESCRIPTION OF ILLUSTRATIVE EMBODIMENTS

In the following detailed description of illustrative embodiments, reference is made to the accompanying drawings that form a part hereof. This detailed description is non-limiting, and the scope of the illustrative embodiments are defined by the appended claims. Other embodiments may be utilized, and logical, structural, mechanical, electrical, and chemical changes may be made without departing from the scope of the appended claims. To avoid detail not necessary to enable those skilled in the art to practice the embodiments described herein, the detailed description may omit certain information known to those skilled in the art. As used herein, unless otherwise indicated, "or" does not require mutual exclusivity.

Figure 1:
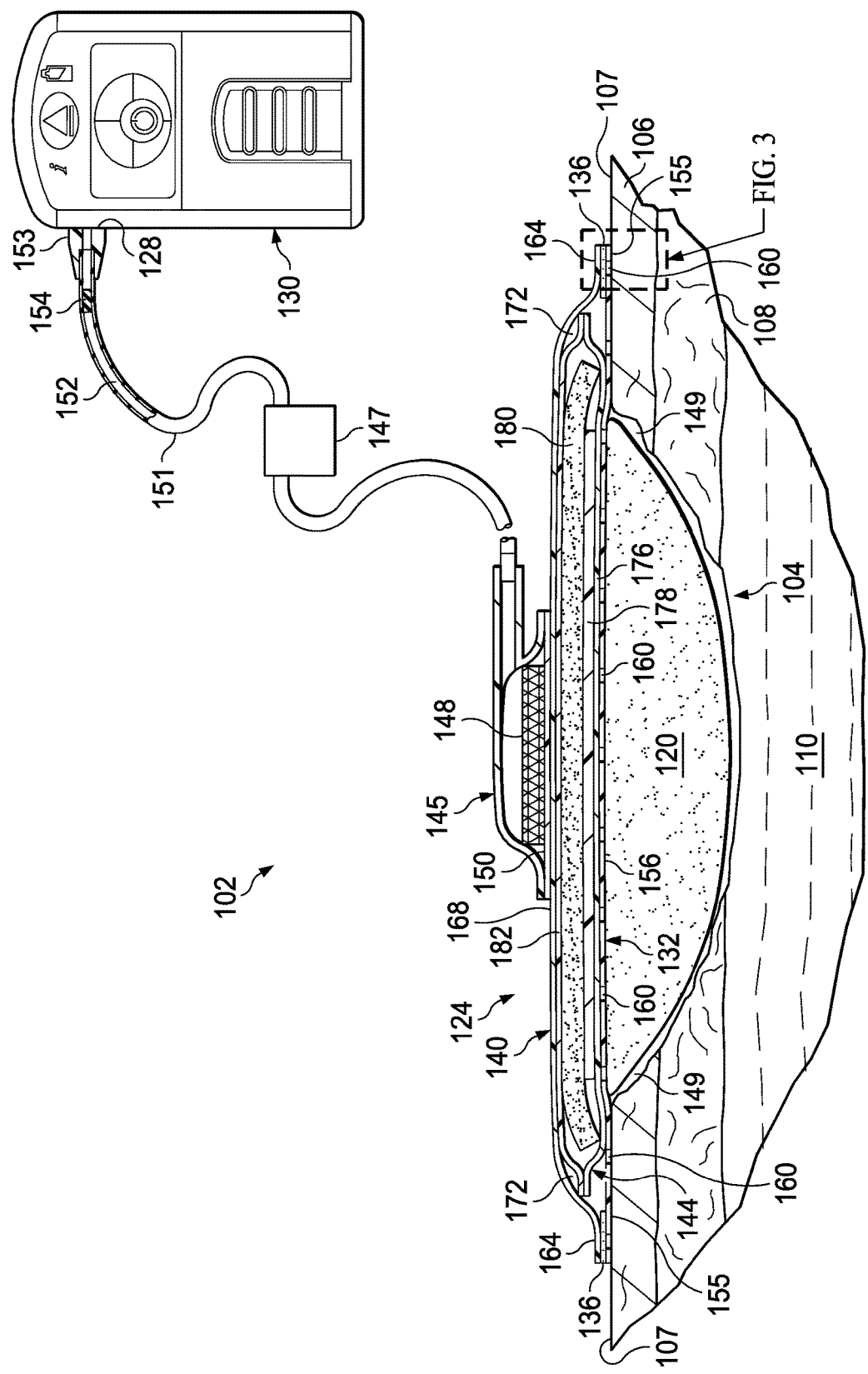
FIG. 1 is a partial cut-away view of an illustrative embodiment of a system for treating a tissue site depicting an illustrative embodiment of a dressing deployed at the tissue site.

Referring to the drawings, FIG. 1 depicts an illustrative embodiment of a system 102 for treating a tissue site 104 of a patient. The tissue site 104 may extend through or otherwise involve an epidermis 106, a dermis 108, and a subcutaneous tissue 110. The tissue site 104 may be a sub-surface tissue site as depicted in FIG. 1 that extends below the surface of the epidermis 106. Further, the tissue site 104 may be a surface tissue site (not shown) that predominantly resides on the surface of the epidermis 106, such as, for example, an incision. The system 102 may provide therapy to, for example, the epidermis 106, the dermis 108, and the subcutaneous tissue 110, regardless of the positioning of the system 102 or the type of tissue site. The system 102 may also be utilized without limitation at other tissue sites.

Further, the tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. The treatment of the tissue site 104 may include the removal of fluids, such as exudate or ascites.

The tissue site 104 may have a periphery 107, such as a boundary, perimeter, or outer region around or surrounding the tissue site 104. The periphery 107 of the tissue site 104 may be tissue or a portion of tissue around or surrounding the tissue site 104 that may be suitable for securing the dressing 124 about the tissue site 104 and capable of supporting a force, such as a compressive, downward, inward or other such force that may be experienced at or directed toward the tissue site 104. As shown in FIG. 1, the periphery 107 of the tissue site 104 may be, for example, the epidermis 106 around or surrounding the tissue site 104. Further, the periphery 107 of the tissue site 104 may be healthy, wound-free, incision-free, or treatment-free tissue that does not require treatment at a given moment around or surrounding the tissue site 104. The illustrative embodiments of the system 102 and the dressing 124 described herein may assist with offloading forces that may be experienced at the tissue site 104 and directing, supporting, or managing these forces in another location, such as at the periphery 107 of the tissue site 104. The offloading of force as described herein may also refer to the removal, reduction, or transfer of force away from a particular location, such as the tissue site 104.

The system 102 may include an optional tissue interface, such as an interface manifold 120, and a dressing 124. Further, the system 102 may include a reduced-pressure source 128, for example, for treatment applications that may benefit from exposure to reduced pressure. The reduced-pressure source 128 may be a component of an optional therapy unit 130 as shown in FIG. 1. In some embodiments, the reduced-pressure source 128 and the therapy unit 130 may be separate components. In other embodiments described further below, the reduced-pressure source 128 may be used without the therapy unit 130.

As indicated above, the interface manifold 120 is an optional component that may be omitted for different types of tissue sites or different types of therapy. If equipped, the interface manifold 120 may be adapted to be positioned proximate to or adjacent to the tissue site 104, such as, for example, by cutting or otherwise shaping the interface manifold 120 in any suitable manner to fit the tissue site 104. As described below, the interface manifold 120 may be adapted to be positioned in fluid communication with the tissue site 104 to distribute reduced pressure to the tissue site 104 or otherwise communicate fluid. In some embodiments, the interface manifold 120 may be positioned in direct contact with the tissue site 104.

The interface manifold 120 may be formed from any manifold material or flexible bolster material that provides a vacuum space, or treatment space, such as, for example, a porous and permeable foam or foam-like material, a member formed with pathways, a graft, or a gauze. Further, any material or combination of materials may be used as a manifold material for the interface manifold 120 provided that the manifold material is operable to distribute or collect fluid across a tissue site. For example, herein the term manifold may refer to a substance or structure capable of delivering fluids to or removing fluids from across a tissue site through a plurality of pores, pathways, or flow channels. The plurality of pores, pathways, or flow channels may be interconnected to improve distribution of fluids provided to and removed from an area around the manifold. Examples of manifolds may include, without limitation, devices that have structural elements arranged to form flow channels, cellular foam, such as open-cell foam, porous tissue collections, and liquids, gels, and foams that include or cure to include flow channels.

In some embodiments, the interface manifold 120 may be a reticulated, open-cell polyurethane or polyether foam that is fluid permeable while under a reduced pressure. One such foam material may be VAC® GranuFoam® material available from Kinetic Concepts, Inc. of San Antonio, Tex. In other embodiments, a material with a higher or lower density than GranuFoam® material may be desirable for the interface manifold 120 depending on the application. Among the many possible materials, the following may be used: GranuFoam® material; Foamex® technical foam (www.foamex.com); a molded bed of nails structure; a patterned grid material, such as those manufactured by Sercol Industrial Fabrics; 3D textiles, such as those manufactured by Baltex of Derby, U.K.; a gauze; a flexible channel-containing member; or a graft; etc. In some embodiments, ionic silver may be added to the interface manifold 120 by, for example, a micro bonding process. Other substances, such as antimicrobial agents, may be added to the interface manifold 120 as well.

In some embodiments, the interface manifold 120 may comprise a porous, hydrophobic material. In such embodiments, the hydrophobic characteristics of the interface manifold 120 may prevent the interface manifold 120 from directly absorbing fluid from the tissue site 104, but allow the fluid to pass through.

Continuing with FIG. 1, in some embodiments, the dressing 124 may include a base layer 132, an adhesive 136, a sealing member 140, and a fluid management assembly 144.

Further, in some embodiments, the dressing 124 may be adapted to provide reduced pressure from the optional reduced-pressure source 128 to the tissue site 104 and/or the optional interface manifold 120, and to store fluid extracted therefrom. For example, in embodiments employing reduced pressure, the dressing 124 may optionally include a conduit interface 145 for providing fluid communication between the reduced-pressure source 128 and the dressing 124. Further, in some embodiments, the dressing 124 may additionally or alternatively be adapted to wick, attract, or otherwise draw fluid into the dressing 124. As described herein, components of the dressing 124 may be added or removed to suit different applications, and usage with or without reduced pressure.

Figure 4:
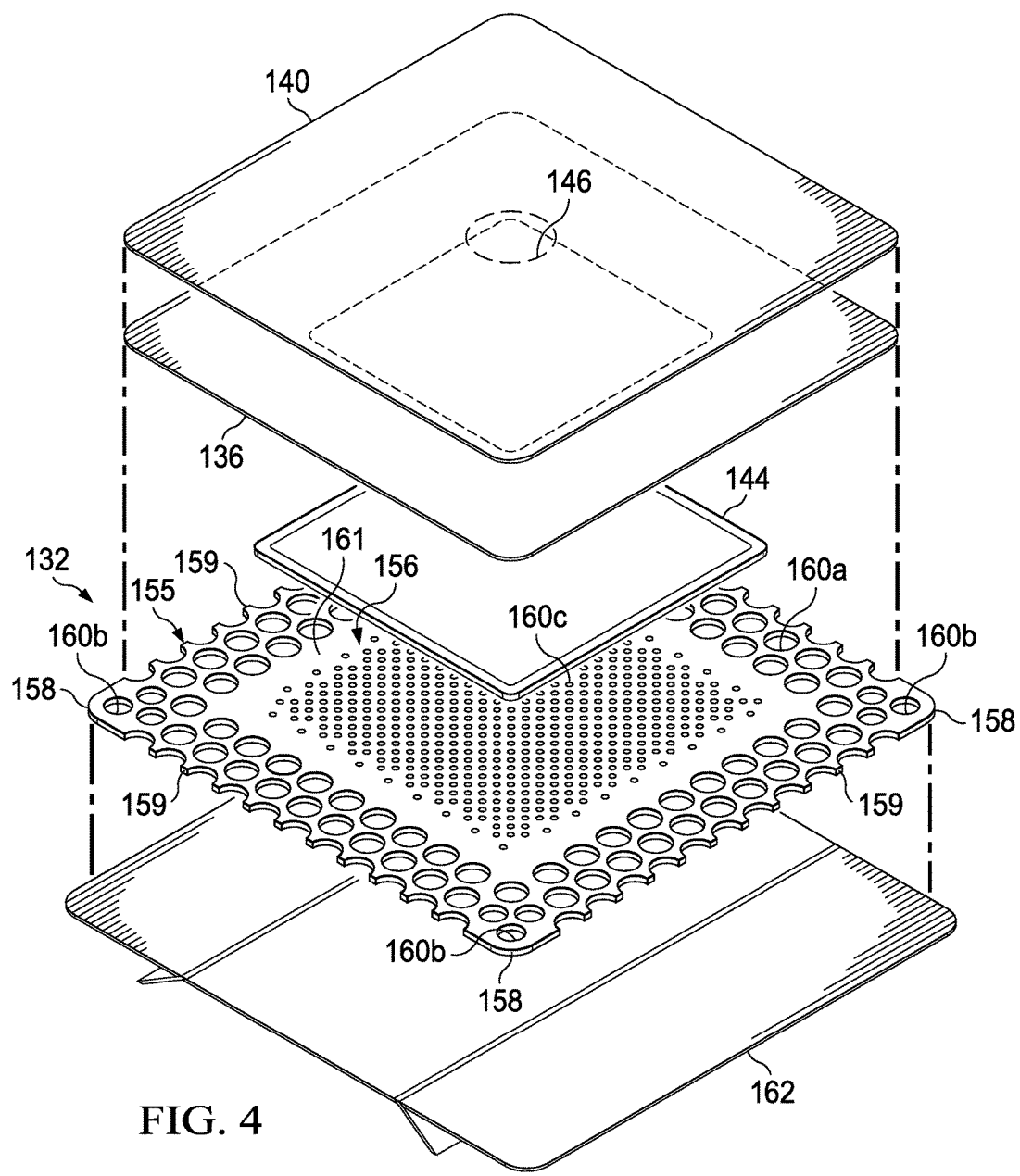
FIG. 4 is an exploded view of the dressing of FIG. 1, depicted without a conduit interface and with an illustrative embodiment of a release liner for protecting the dressing prior to application at a tissue site.

The conduit interface 145 may be positioned proximate to the sealing member 140 and in fluid communication with the dressing 124 and the components thereof, for example, through an aperture 146, shown in dash line in FIG. 4, that may be disposed through the sealing member 140. The conduit interface 145 may provide reduced pressure from the reduced-pressure source 128 to the dressing 124 through the aperture 146. In some embodiments, the conduit interface 145 may also be positioned in fluid communication with the optional interface manifold 120. Further, in some embodiments, an optional liquid trap 147 may be positioned in fluid communication between the dressing 124 and the reduced-pressure source 128. The liquid trap 147 may be any suitable containment device having a sealed internal volume capable of retaining liquid, such as condensate or other liquids, as described below.

The conduit interface 145 may comprise a medical-grade, soft polymer or other pliable material. As non-limiting examples, the conduit interface 145 may be formed from polyurethane, polyethylene, polyvinyl chloride (PVC), fluorosilicone, or ethylene-propylene, etc. In some embodiments, conduit interface 145 may be molded from DEHP-free PVC. The conduit interface 145 may be formed in any suitable manner, such as, without limitation, by molding, casting, machining, or extruding. Further, the conduit interface 145 may be formed as an integral unit or as individual components, and the conduit interface 145 may be coupled to the dressing 124 by, for example, adhesive or welding.

In some embodiments, the conduit interface 145 may be formed of an absorbent material having absorbent and evaporative properties. The absorbent material may be vapor permeable and liquid impermeable, thereby being configured to permit vapor to be absorbed into and evaporated from the material through permeation while inhibiting the permeation of liquids. The absorbent material may be, for example, a hydrophilic polymer such as a hydrophilic polyurethane. Although the term hydrophilic polymer may be used in the illustrative embodiments that follow, any absorbent material having the properties described herein may be suitable for use in the system 102. Further, the absorbent material or hydrophilic polymer may be suitable for use in various components of the system 102 as described herein.

The use of such a hydrophilic polymer for the conduit interface 145 may permit any liquids in the conduit interface 145 to evaporate, or otherwise dissipate, during operation. For example, the hydrophilic polymer may allow the liquid to permeate or pass through the conduit interface 145 as vapor, in a gaseous phase, and evaporate into the atmosphere external to the conduit interface 145. Such liquids may be, for example, condensate or other liquids. Condensate may form, for example, as a result of a decrease in temperature within the conduit interface 145, or other components of the system 102, relative to the temperature at the tissue site 104. The removal or dissipation of liquids from the conduit interface 145 may increase visual appeal and prevent odor. Further, such removal of liquids may also increase efficiency and reliability by reducing blockages and other interference with the components of the system 102.

Similar to the conduit interface 145, the liquid trap 147, and other components of the system 102 described herein, may also be formed of an absorbent material or a hydrophilic polymer. The absorptive and evaporative properties of the hydrophilic polymer may also facilitate removal and dissipation of liquids that may reside in the liquid trap 147, and other components of the system 102, by evaporation. Such evaporation may leave behind a substantially solid or gel-like waste. The substantially solid or gel-like waste may be cheaper to dispose than liquids, providing a cost savings for operation of the system 102. The hydrophilic polymer may be used for other components in the system 102 where the management of liquids is beneficial.

In some embodiments, the absorbent material or hydrophilic polymer may have an absorbent capacity in a saturated state that is substantially equivalent to the mass of the hydrophilic polymer in an unsaturated state. The hydrophilic polymer may be fully saturated with vapor in the saturated state and substantially free of vapor in the unsaturated state. In both the saturated state and the unsaturated state, the hydrophilic polymer may retain substantially the same physical, mechanical, and structural properties. For example, the hydrophilic polymer may have a hardness in the unsaturated state that is substantially the same as a hardness of the hydrophilic polymer in the saturated state. The hydrophilic polymer and the components of the system 102 incorporating the hydrophilic polymer may also have a size that is substantially the same in both the unsaturated state and the saturated state. Further, the hydrophilic polymer may remain dry, cool to the touch, and pneumatically sealed in the saturated state and the unsaturated state. The hydrophilic polymer may also remain substantially the same color in the saturated state and the unsaturated state. In this manner, this hydrophilic polymer may retain sufficient strength and other physical properties to remain suitable for use in the system 102. An example of such a hydrophilic polymer is offered under the trade name Techophilic HP-93A-100, available from The Lubrizol Corporation of Wickliffe, Ohio, United States. Techophilic HP-93A-100 is an absorbent hydrophilic thermoplastic polyurethane capable of absorbing 100% of the unsaturated mass of the polyurethane in water and having a durometer or Shore Hardness of about 83 Shore A.

The conduit interface 145 may carry an odor filter 148 adapted to substantially preclude the passage of odors from the tissue site 104 out of a sealed space 149 provided by the sealing member 140. Further, the conduit interface 145 may carry a primary hydrophobic filter 150 adapted to substantially preclude the passage of liquids out of the sealed space 149. The odor filter 148 and the primary hydrophobic filter 150 may be disposed in the conduit interface 145 or other suitable location such that fluid communication between the reduced-pressure source 128, or optional therapy unit 130, and the dressing 124 is provided through the odor filter 148 and the primary hydrophobic filter 150. In some embodiments, the odor filter 148 and the primary hydrophobic filter 150 may be secured within the conduit interface 145 in any suitable manner, such as by adhesive or welding. In other embodiments, the odor filter 148 and the primary hydrophobic filter 150 may be positioned in any exit location in the dressing 124 that is in fluid communication with the atmosphere, the reduced-pressure source 128, or the optional therapy unit 130. The odor filter 148 may also be positioned in any suitable location in the system 102 that is in fluid communication with the tissue site 104.

The odor filter 148 may be comprised of a carbon material in the form of a layer or particulate. For example, in some embodiments, the odor filter 148 may comprise a woven carbon cloth filter such as those manufactured by Chemviron Carbon, Ltd. of Lancashire, United Kingdom (www.chemvironcarbon.com). The primary hydrophobic filter 150 may be comprised of a material that is liquid impermeable and vapor permeable. For example, in some embodiments, the primary hydrophobic filter 150 may comprise a material manufactured under the designation MMT-314 by W.L. Gore & Associates, Inc. of Newark, Del., United States, or similar materials. Further, in some embodiments, the primary hydrophobic filter 150 may be provided in the form of a membrane or layer.

Continuing with FIG. 1, in embodiments that use reduced pressure, the reduced-pressure source 128 may provide reduced pressure to the dressing 124 and the sealed space 149. The reduced-pressure source 128 may be any suitable device for providing reduced pressure, such as, for example, a vacuum pump, wall suction, hand pump, or other source. As shown in FIG. 1, in some embodiments, the reduced-pressure source 128 may be a component of the therapy unit 130. The therapy unit 130 may include control circuitry and sensors, such as a pressure sensor, that may be configured to monitor reduced pressure at the tissue site 104. In some embodiments, the therapy unit 130 may also be configured to control the amount of reduced pressure from the reduced-pressure source 128 being applied to the tissue site 104 according to a user input and a reduced-pressure feedback signal received from the tissue site 104.

As used herein, reduced pressure may refer to a pressure less than the ambient pressure at a tissue site being subjected to treatment. The reduced pressure may be less than the atmospheric pressure, and may also be less than a hydrostatic pressure at a tissue site. Unless otherwise indicated, values of pressure stated herein are gauge pressures. While the amount and nature of reduced pressure applied to a tissue site may vary according to the application, in some embodiments, the reduced pressure may be between about −5 mm Hg to about −500 mm Hg. In some embodiments, the reduced pressure may be between about −100 mm Hg to about −200 mm Hg.

The reduced pressure may be constant, varied, patterned, or random, and may be delivered continuously or intermittently. Although the terms vacuum and negative pressure may be used to describe the pressure applied to the tissue site, the actual pressure applied to the tissue site may be more than the pressure normally associated with a complete vacuum. Consistent with the use herein, an increase in reduced pressure or vacuum pressure may refer to a relative reduction in absolute pressure. For example, an increase in reduced pressure may correspond to a reduction in pressure (more negative relative to ambient pressure) and a decrease in reduced pressure may correspond to an increase in pressure (less negative relative to ambient pressure).

As shown in FIG. 1, a conduit 151 having an internal lumen 152 may be coupled in fluid communication between the reduced-pressure source 128 and the dressing 124. In some embodiments, the internal lumen 152 may have an internal diameter between about 0.5 millimeters to about 3.0 millimeters. In other embodiments, the internal diameter of the internal lumen 152 may be between about 1 millimeter to about 2 millimeters. The conduit interface 145 may be coupled in fluid communication with the dressing 124 and adapted to connect between the conduit 151 and the dressing 124 for providing fluid communication with the reduced-pressure source 128. The conduit interface 145 may be fluidly coupled to the conduit 151 in any suitable manner, such as, for example, by an adhesive, solvent or non-solvent bonding, welding, or interference fit. As described above, the aperture 146 in the sealing member 140 may provide fluid communication between the dressing 124 and the conduit interface 145. In some embodiments, the conduit interface 145 may be in fluid communication with the sealed space 149 through the aperture 146 in the sealing member 140. In other embodiments, the conduit 151 may be inserted into the dressing 124 through the sealing member 140, or through the aperture 146 in the sealing member 140, in any suitable manner to provide fluid communication with the reduced-pressure source 128 without use of the conduit interface 145. The reduced-pressure source 128 may also be directly coupled in fluid communication with the dressing 124 or the sealing member 140 without use of the conduit 151. The conduit 151 may be, for example, a flexible polymer tube. A distal end of the conduit 151 may include a coupling 153 for attachment to the reduced-pressure source 128.

The conduit 151 may have a secondary hydrophobic filter 154 disposed in the internal lumen 152 such that fluid communication between the reduced-pressure source 128 and the dressing 124 is provided through the secondary hydrophobic filter 154. The secondary hydrophobic filter 154 may be, for example, a porous, sintered polymer cylinder sized to fit the dimensions of the internal lumen 152 to substantially preclude liquid from bypassing the cylinder. The secondary hydrophobic filter 154 may also be treated with an absorbent material adapted to swell when brought into contact with liquid to block the flow of the liquid. The secondary hydrophobic filter 154 may be positioned at any location within the internal lumen 152. However, positioning the secondary hydrophobic filter 154 within the internal lumen 152 closer toward the reduced-pressure source 128, rather than the dressing 124, may allow a user to detect the presence of liquid in the internal lumen 152.

In some embodiments, the conduit 151 and the coupling 153 may be formed of an absorbent material or a hydrophilic polymer as described above for the conduit interface 145. In this manner, the conduit 151 and the coupling 153 may permit liquids in the conduit 151 and the coupling 153 to evaporate, or otherwise dissipate, as described above for the conduit interface 145. The conduit 151 and the coupling 153 may be, for example, molded from the hydrophilic polymer separately, as individual components, or together as an integral component. Further, a wall of the conduit 151 defining the internal lumen 152 may be extruded from the hydrophilic polymer. In some embodiments, the conduit 151 may be less than about 1 meter in length, but may have any length to suit a particular application. A length of about 1 foot or 304.8 millimeters for the conduit 151 may provide enough absorbent and evaporative surface area to suit many applications, and may provide a cost savings compared to longer lengths. If an application requires additional length for the conduit 151, the absorbent hydrophilic polymer may be coupled in fluid communication with a length of conduit formed of a non-absorbent hydrophobic polymer to provide additional cost savings.

Referring to FIGS. 2-5, the base layer 132 may have a periphery 155 surrounding or around a central portion 156, and a plurality of apertures 160 disposed through the periphery 155 and the central portion 156. The base layer 132 may also have corners 158 and edges 159. The corners 158 and the edges 159 may be part of the periphery 155. One of the edges 159 may meet another of the edges 159 to define one of the corners 158. Further, the base layer 132 may have a border 161 substantially surrounding the central portion 156 and positioned between the central portion 156 and the periphery 155. The border 161 may be free of the apertures 160. The base layer 132 may be adapted to cover the tissue site 104, the optional interface manifold 120, and tissue around or surrounding the tissue site 104. The central portion 156 of the base layer 132 may be positioned adjacent to, proximate to, or covering the tissue site 104 and the optional interface manifold 120. The periphery 155 of the base layer 132 may be positioned adjacent to or proximate to tissue around or surrounding the tissue site 104. In this manner, the periphery 155 of the base layer 132 may be positioned around or surrounding the tissue site 104 and the optional interface manifold 120. Further, the apertures 160 in the base layer 132 may be in fluid communication with the tissue site 104, the optional interface manifold 120, and tissue surrounding the tissue site 104.

Figure 5:
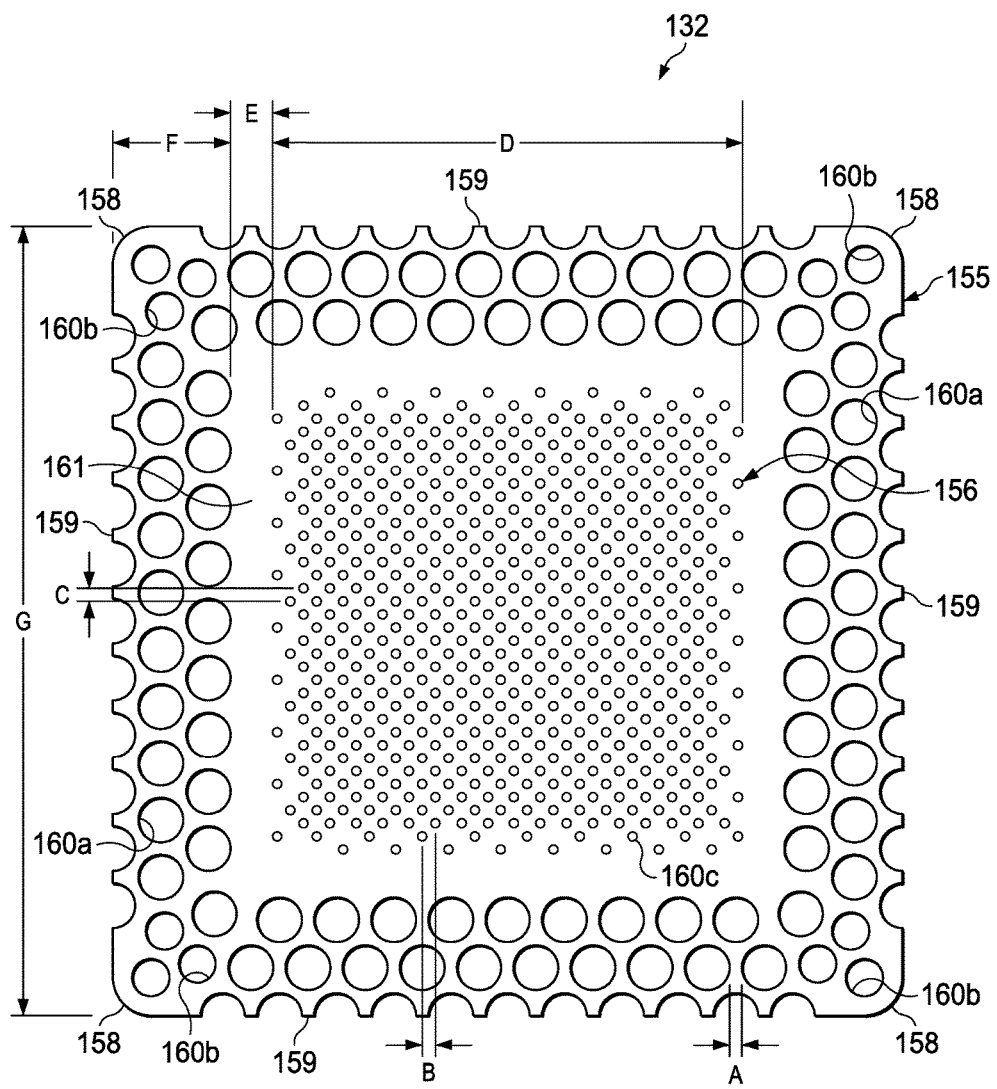
FIG. 5 is a plan view of an illustrative embodiment of a base layer depicted in FIG. 4.

The apertures 160 in the base layer 132 may have any shape, such as, for example, circles, squares, stars, ovals, polygons, slits, complex curves, rectilinear shapes, triangles, or other shapes. The apertures 160 may be formed by cutting, by application of local RF energy, or other suitable techniques for forming an opening. As shown in FIGS. 4-5, in some embodiments, each of the apertures 160 of the plurality of apertures 160 may be substantially circular in shape, having a diameter and an area. The area of each of the apertures 160 may refer to an open space or open area defining each of the apertures 160. The diameter of each of the apertures 160 may define the area of each of the apertures 160. For example, the area of one of the apertures 160 may be defined by multiplying the square of half the diameter of the aperture 160 by the value 3.14. Thus, the following equation may define the area of one of the apertures 160: Area=3.14*(diameter/2)^2.

The area of the apertures 160 described in the illustrative embodiments herein may be substantially similar to the area in other embodiments (not shown) for the apertures 160 that may have non-circular shapes. The diameter of each of the apertures 160 may be substantially the same, or each of the diameters may vary depending, for example, on the position of the aperture 160 in the base layer 132. For example, in some embodiments, the diameter of the apertures 160 in the periphery 155 of the base layer 132 may be larger than the diameter of the apertures 160 in the central portion 156 of the base layer 132. In some embodiments, the diameter of each of the apertures 160 may be between about 1 millimeter to about 50 millimeters. In other embodiments, the diameter of each of the apertures 160 may be between about 1 millimeter to about 20 millimeters. The apertures 160 may have a uniform pattern or may be randomly distributed on the base layer 132. The size and configuration of the apertures 160 may be designed to control the adherence of the dressing 124 to the epidermis 106 as described below.

Referring to FIGS. 4-5, the apertures 160 positioned in the periphery 155 may be apertures 160a, the apertures 160 positioned at the corners 158 of the periphery 155 may be apertures 160b, and the apertures 160 positioned in the central portion 156 may be apertures 160c. In some embodiments, the apertures 160a may have a diameter between about 9.8 millimeters to about 10.2 millimeters. In some embodiments, the apertures 160b may have a diameter between about 7.75 millimeters to about 8.75 millimeters. In some embodiments, the apertures 160c may have a diameter between about 1.8 millimeters to about 2.2 millimeters. Other dimensions and sizes for the apertures 160 are possible.

In some embodiments, the diameter of each of the apertures 160a may be separated from one another by a distance A between about 2.8 millimeters to about 3.2 millimeters. Further, the diameter of at least one of the apertures 160a may be separated from the diameter of at least one of the apertures 160b by the distance A. The diameter of each of the apertures 160b may also be separated from one another by the distance A. A center of one of the apertures 160c may be separated from a center of another of the apertures 160c in a first direction by a distance B between about 2.8 millimeters to about 3.2 millimeters. In a second direction transverse to the first direction, the center of one of the apertures 160c may be separated from the center of another of the apertures 160c by a distance C between about 2.8 millimeters to about 3.2 millimeters. As shown in FIGS. 4-5, the distance B and the distance C may be increased for the apertures 160c in the central portion 156 being positioned proximate to or at the border 161 compared to the apertures 160c positioned away from the border 161.

Continuing with FIGS. 4-5, in some embodiments, the central portion 156 of the base layer 132 may be substantially square with each side of the central portion 156 having a length D between about 100 millimeters to about 108 millimeters. In some embodiments, the length D may be between about 106 millimeters to about 108 millimeters. Further, the border 161 of the base layer 132 may have a width E between about 4 millimeters to about 11 millimeters, and may substantially surround the central portion 156 and the apertures 160c in the central portion 156. In some embodiments, the width E may be between about 9 millimeters to about 10 millimeters. Further, the periphery 155 of the base layer 132 may have a width F between about 25 millimeters to about 35 millimeters, and may substantially surround the border 161 and the central portion 156. In some embodiments, the width F may be between about 26 millimeters to about 28 millimeters. Further, the periphery 155 may have a substantially square exterior with each side of the exterior having a length G between about 154 millimeters to about 200 millimeters. In some embodiments, the length G may be between about 176 millimeters to about 184 millimeters.

Although FIGS. 4-5 depict the central portion 156, the border 161, and the periphery 155 of the base layer 132 as having a substantially square shape, these and other components of the base layer 132 and the dressing 124 may have any shape to suit a particular application or anatomical location. Further, the dimensions of the base layer 132 as described herein may be increased or decreased, for example, substantially in proportion to one another to suit a particular application. The use of the dimensions in the proportions described above may enhance the cosmetic appearance of a tissue site. For example, these proportions may provide a surface area for the base layer 132, regardless of shape, that is sufficiently smooth to enhance the movement and proliferation of epithelial cells at the tissue site 104, and reduce the likelihood of granulation tissue in-growth into the dressing 124.

The base layer 132 may be a soft, pliable material suitable for providing a fluid seal with the tissue site 104 as described herein. For example, the base layer 132 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive described below, polyurethane, polyolefin, or hydrogenated styrenic copolymers. In some embodiments, the base layer 132 may have a thickness between about 500 microns (μm) and about 1000 microns (μm). In some embodiments, the base layer 132 may have a stiffness between about 5 Shore OO and about 80 Shore OO. Further, the base layer 132 may be comprised of hydrophobic or hydrophilic materials.

In some embodiments (not shown), the base layer 132 may be a hydrophobic-coated material. For example, the base layer 132 may be formed by coating a spaced material, such as, for example, woven, nonwoven, molded, or extruded mesh with a hydrophobic material. The hydrophobic material for the coating may be a soft silicone, for example. In this manner, the adhesive 136 may extend through openings in the spaced material analogous to the apertures 160 as described below.

Continuing with FIGS. 4-5 with reference to the detail view of FIG. 3, the adhesive 136 may be in fluid communication with the apertures 160 in at least the periphery 155 of the base layer 132. In this manner, the adhesive 136 may be in fluid communication with the tissue around or surrounding the tissue site 104 through the apertures 160 in the base layer 132. As described below and shown in the detail view of FIG. 3, the adhesive 136 may extend or be pressed through the plurality of apertures 160 to contact the epidermis 106 for securing the dressing 124 to, for example, the tissue around or surrounding the tissue site 104. The apertures 160 may provide sufficient contact of the adhesive 136 to the epidermis 106 to secure the dressing 124 about the tissue site 104. However, the configuration of the apertures 160 and the adhesive 136, described below, may permit release and repositioning of the dressing 124 about the tissue site 104.

At least one of the apertures 160*a* in the periphery 155 of the base layer 132 may be positioned at the edges 159 of the periphery 155, and may have an interior cut open or exposed at the edges 159 that is in fluid communication in a lateral direction with the edges 159. The lateral direction may refer to a direction toward the edges 159 and in the same plane as the base layer 132. As shown in FIGS. 4-5, a plurality of the apertures 160*a* in the periphery 155 may be positioned proximate to or at the edges 159 and in fluid communication in a lateral direction with the edges 159. The apertures 160*a* positioned proximate to or at the edges 159 may be spaced substantially equidistant around the periphery 155 as shown in FIGS. 4-5. However, in some embodiments, the spacing of the apertures 160*a* proximate to or at the edges 159 may be irregular. The adhesive 136 may be in fluid communication with the edges 159 through the apertures 160*a* being exposed at the edges 159. In this manner, the apertures 160*a* at the edges 159 may permit the adhesive 136 to flow around the edges 159 for enhancing the adhesion of the edges 159 around the tissue site 104, for example.

Continuing with FIGS. 4-5, the apertures 160*b* at the corners 158 of the periphery 155 may be smaller than the apertures 160*a* in other portions of the periphery 155 as described above. For a given geometry of the corners 158, the smaller size of the apertures 160*b* compared to the apertures 160*a* may maximize the surface area of the adhesive 136 exposed and in fluid communication through the apertures 160*b* at the corners 158. For example, as shown in FIGS. 4-5, the edges 159 may intersect at substantially a right angle, or about 90 degrees, to define the corners 158. In some embodiments, the corners 158 may have a radius of about 10 millimeters. Further, in some embodiments, three of the apertures 160*b* having a diameter between about 7.75 millimeters to about 8.75 millimeters may be positioned in a triangular configuration at the corners 158 to maximize the exposed surface area for the adhesive 136. In other embodiments, the size and number of the apertures 160*b* in the corners 158 may be adjusted as necessary, depending on the chosen geometry of the corners 158, to maximize the exposed surface area of the adhesive 136 as described above. Further, the apertures 160*b* at the corners 158 may be fully housed within the base layer 132, substantially precluding fluid communication in a lateral direction exterior to the corners 158. The apertures 160*b* at the corners 158 being fully housed within the base layer 132 may substantially preclude fluid communication of the adhesive 136 exterior to the corners 158, and may provide improved handling of the dressing 124 during deployment at the tissue site 104. Further, the exterior of the corners 158 being substantially free of the adhesive 136 may increase the flexibility of the corners 158 to enhance comfort.

Similar to the apertures 160*b* in the corners 158, any of the apertures 160 may be adjusted in size and number to maximize the surface area of the adhesive 136 in fluid communication through the apertures 160 for a particular application or geometry of the base layer 132. For example, in some embodiments (not shown) the apertures 160*b*, or apertures of another size, may be positioned in the periphery 155 and at the border 161. Similarly, the apertures 160*b*, or apertures of another size, may be positioned as described above in other locations of the base layer 132 that may have a complex geometry or shape.

The adhesive 136 may be a medically-acceptable adhesive. The adhesive 136 may also be flowable. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive with coating weight of about 15 grams/m$^2$ (gsm) to about 70 grams/m$^2$ (gsm). The adhesive 136 may be a layer having substantially the same shape as the periphery 155 of the base layer 132 as shown in FIG. 4. In some embodiments, the layer of the adhesive 136 may be continuous or discontinuous. Discontinuities in the adhesive 136 may be provided by apertures or holes (not shown) in the adhesive 136. The apertures or holes in the adhesive 136 may be formed after application of the adhesive 136 or by coating the adhesive 136 in patterns on a carrier layer, such as, for example, a side of the sealing member 140 adapted to face the epidermis 106. Further, the apertures or holes in the adhesive 136 may be sized to control the amount of the adhesive 136 extending through the apertures 160 in the base layer 132 to reach the epidermis 106. The apertures or holes in the adhesive 136 may also be sized to enhance the Moisture Vapor Transfer Rate (MVTR) of the dressing 124, described further below.

Factors that may be utilized to control the adhesion strength of the dressing 124 may include the diameter and number of the apertures 160 in the base layer 132, the thickness of the base layer 132, the thickness and amount of the adhesive 136, and the tackiness of the adhesive 136. An increase in the amount of the adhesive 136 extending through the apertures 160 may correspond to an increase in the adhesion strength of the dressing 124. A decrease in the thickness of the base layer 132 may correspond to an increase in the amount of the adhesive 136 extending through the apertures 160. Thus, the diameter and configuration of the apertures 160, the thickness of the base layer 132, and the amount and tackiness of the adhesive utilized may be varied to provide a desired adhesion strength for the dressing 124. For example, in some embodiments, the thickness of the base layer 132 may be about 200 microns, the adhesive 136 may have a thickness of about 30 microns and a tackiness of 2000 grams per 25 centimeter wide strip, and the diameter of the apertures 160a in the base layer 132 may be about 10 millimeters.

In some embodiments, the tackiness of the adhesive 136 may vary in different locations of the base layer 132. For example, in locations of the base layer 132 where the apertures 160 are comparatively large, such as the apertures 160a, the adhesive 136 may have a lower tackiness than other locations of the base layer 132 where the apertures 160 are smaller, such as the apertures 160b and 160c. In this manner, locations of the base layer 132 having larger apertures 160 and lower tackiness adhesive 136 may have an adhesion strength comparable to locations having smaller apertures 160 and higher tackiness adhesive 136.

Clinical studies have shown that the configuration described herein for the base layer 132 and the adhesive 136 may reduce the occurrence of blistering, erythema, and leakage when in use. Such a configuration may provide, for example, increased patient comfort and increased durability of the dressing 124.

Referring to FIG. 4, a release liner 162 may be attached to or positioned adjacent to the base layer 132 to protect the adhesive 136 prior to application of the dressing 124 to the tissue site 104. Prior to application of the dressing 124 to the tissue site 104, the base layer 132 may be positioned between the sealing member 140 and the release liner 162. Removal of the release liner 162 may expose the base layer 132 and the adhesive 136 for application of the dressing 124 to the tissue site 104. The release liner 162 may also provide stiffness to assist with, for example, deployment of the dressing 124. The release liner 162 may be, for example, a casting paper, a film, or polyethylene. Further, in some embodiments, the release liner 162 may be a polyester material such as polyethylene terephthalate (PET), or similar polar semi-crystalline polymer. The use of a polar semi-crystalline polymer for the release liner 162 may substantially preclude wrinkling or other deformation of the dressing 124. For example, the polar semi-crystalline polymer may be highly orientated and resistant to softening, swelling, or other deformation that may occur when brought into contact with components of the dressing 124, or when subjected to temperature or environmental variations, or sterilization. Further, a release agent may be disposed on a side of the release liner 162 that is configured to contact the base layer 132. For example, the release agent may be a silicone coating and may have a release factor suitable to facilitate removal of the release liner 162 by hand and without damaging or deforming the dressing 124. In some embodiments, the release agent may be fluorosilicone. In other embodiments, the release liner 162 may be uncoated or otherwise used without a release agent.

Referring to FIGS. 1-3, the sealing member 140 may have a periphery 164 and a central portion 168. The periphery 164 of the sealing member 140 may be positioned proximate to the periphery 155 of the base layer 132, and the central portion 168 of the sealing member 140 and the central portion 156 of the base layer 132 may define a dressing enclosure 172. The adhesive 136 may be positioned at least between the periphery 164 of the sealing member 140 and the periphery 155 of the base layer 132. The sealing member 140 may cover the tissue site 104 and the interface manifold 120 to provide a fluid seal and the sealed space 149 between the tissue site 104 and the sealing member 140 of the dressing 124. Further, the sealing member 140 may cover other tissue, such as a portion of the epidermis 106, around or surrounding the tissue site 104 to provide the fluid seal between the sealing member 140 and the tissue site 104. In some embodiments, a portion of the periphery 164 of the sealing member 140 may extend beyond the periphery 155 of the base layer 132 and into direct contact with tissue around or surrounding the tissue site 104. In other embodiments, the periphery 164 of the sealing member 140, for example, may be positioned in contact with tissue around or surrounding the tissue site 104 to provide the sealed space 149 without the base layer 132. Thus, the adhesive 136 may also be positioned at least between the periphery 164 of the sealing member 140 and tissue, such as the epidermis 106, surrounding the tissue site 104. The adhesive 136 may be disposed on a surface of the sealing member 140 adapted to face the tissue site 104 and the base layer 132.

The sealing member 140 may be formed from any material that allows for a fluid seal. A fluid seal may be a seal adequate to maintain reduced pressure at a desired site given the particular reduced pressure source or system involved. The sealing member 140 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; Expopack 2327; or other appropriate material.

The sealing member 140 may be vapor permeable and liquid impermeable, thereby allowing vapor and inhibiting liquids from exiting the sealed space 149 provided by the dressing 124. In some embodiments, the sealing member 140 may be a flexible, breathable film, membrane, or sheet having a high MVTR of, for example, at least about 300 g/m$^2$ per 24 hours. In other embodiments, a low or no vapor transfer drape might be used. The sealing member 140 may comprise a range of medically suitable films having a thickness between about 15 microns (μm) to about 50 microns (μm).

Figure 6:
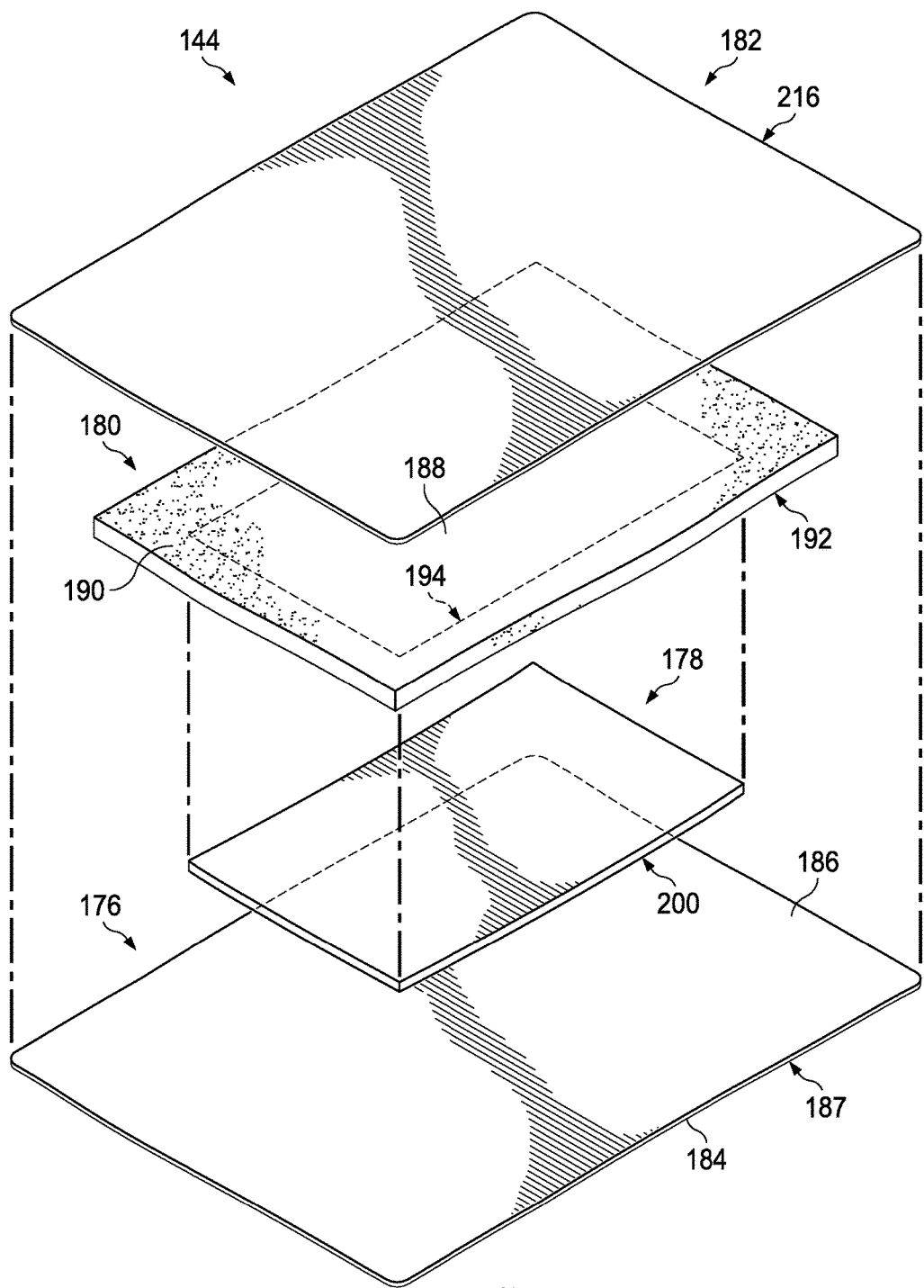
FIG. 6 is an exploded view of an illustrative embodiment of a fluid management assembly depicted in FIG. 4.

Referring to FIG. 6, in some embodiments, the fluid management assembly 144 may include a fluid transport layer 176, a liquid deflector 178, and an offloading layer 180. In some embodiments, the fluid management assembly 144 may optionally include an enclosing layer 182. The fluid transport layer 176, the offloading layer 180, and the liquid deflector 178 may each be adapted to be positioned within the sealed space 149. Further, in some embodiments, the fluid management assembly 144 may be disposed in the dressing enclosure 172 as shown in FIGS. 1-2.

The fluid management assembly 144 may be a pre-laminated structure manufactured at a single location or individual layers of material stacked upon one another as described herein. Individual layers of the fluid management assembly 144 may be bonded or otherwise secured to one another without adversely affecting fluid management by, for example, utilizing a solvent or non-solvent adhesive, or by thermal welding. Further, the fluid management assembly 144 may be coupled to the border 161 of the base layer 132 in any suitable manner, such as, for example, by a weld or an adhesive. The border 161 being free of the apertures 160 as described above may provide a flexible barrier between the fluid management assembly 144 and the tissue site 104 for enhancing comfort.

The fluid transport layer 176 may include a first side 184 and a second side 186 in fluid communication with the tissue site 104, and a periphery 187. The first side 184 of the fluid transport layer 176 may be adapted to be positioned facing the tissue site 104. In some embodiments, the fluid transport layer 176 may be positioned between the base layer 132 and the sealing member 140. The fluid transport layer 176 may be adapted to provide fluid communication with the tissue site 104, and to wick liquid from the tissue site 104 along the fluid transport layer 176 in a lateral direction normal to a thickness of the fluid transport layer 176. For example, the fluid transport layer 176 may wick or otherwise transport liquid in a lateral direction along a surface of the fluid transport layer 176, such as the first side 184 and/or the second side 186. The lateral direction may be parallel to the first side 184 and/or the second side 186. The surface of the fluid transport layer 176 may be normal relative to the thickness of fluid transport layer 176. The wicking of liquid along the fluid transport layer 176 may enhance the distribution of liquid to the offloading layer 180.

The fluid transport layer 176 may comprise a fluid permeable material that may be a non-woven. In some embodiments, the fluid transport layer 176 may comprise a polyester fibrous and porous structure. Further, in some embodiments, the first side 184 of the fluid transport layer 176 maybe a hydrophilic side, and the second side 186 of the fluid transport layer 176 may be a hydrophobic side. For example, the hydrophilic side of the fluid transport layer 176 may comprise a fibrous surface adapted to acquire the liquid from the tissue site 104 for moving or drawing liquid through the fluid transport layer 176 and toward the offloading layer 180. The hydrophilic side may also be referred to as a fluid acquisition surface, fluid acquisition side, hydrophilic acquisition surface, or hydrophilic acquisition side. The hydrophobic side of the fluid transport layer 176 may comprise a directional grain (not shown) adapted to wick or distribute the liquid along the directional grain. The hydrophobic side may also be referred to as a wicking side, wicking surface, distribution surface, distribution side, or fluid distribution surface. The hydrophobic side may have a smooth texture relative to the fibrous texture of the hydrophilic side.

Materials that may be suitable for the fluid transport layer 176 may include any material having a directional grain structure capable of wicking fluid as described herein, such as, for example, LIBELTEX TDL2 or LIBELTEX TL4. The fluid transport layer 176 may have a material density between about 80 gsm to about 150 gsm. In other embodiments, the material density may be lower or greater depending on the particular application or need.

The offloading layer 180 may be positioned in fluid communication with the fluid transport layer 176. In some embodiments, the offloading layer 180 may be positioned in fluid communication between the fluid transport layer 176 and the optional enclosing layer 182. The offloading layer 180 may include a force offloading region 188, a target region 190, and a periphery 192. The target region 190 of the offloading layer 180 may be adapted to expand in thickness upon contact with liquid from the tissue site 104, while the force offloading region 188 of the offloading layer 180 may be adapted to be substantially free of expansion and contact with the liquid.

The force offloading region 188 may be adapted to cover the tissue site 104, and the target region 190 may be adapted to be positioned at or around the periphery 107 of the tissue site 104. In some embodiments, the target region 190 may be positioned around the force offloading region 188. Further, in some embodiments, the target region 190 may be positioned at a periphery 194 of the force offloading region 188.

The offloading layer 180 may comprise an absorbent material or hydrophilic material, such as, for example a super absorbent polymer capable of absorbing liquid that may be associated with the tissue site 104. Materials that may be suitable for the offloading layer 180 may include, without limitation, Luquafleece® material; Texsus FP2326; BASF 402C; Technical Absorbents 2317, available from Technical Absorbents; sodium polyacrylate super absorbers; cellulosics (carboxy methyl cellulose and salts such as sodium CMC); alginates; or any combination of such materials. Further, the offloading layer 180 may comprise a material that may be, without limitation, foam, mesh, non-woven, or granular in nature.

Figure 7A:
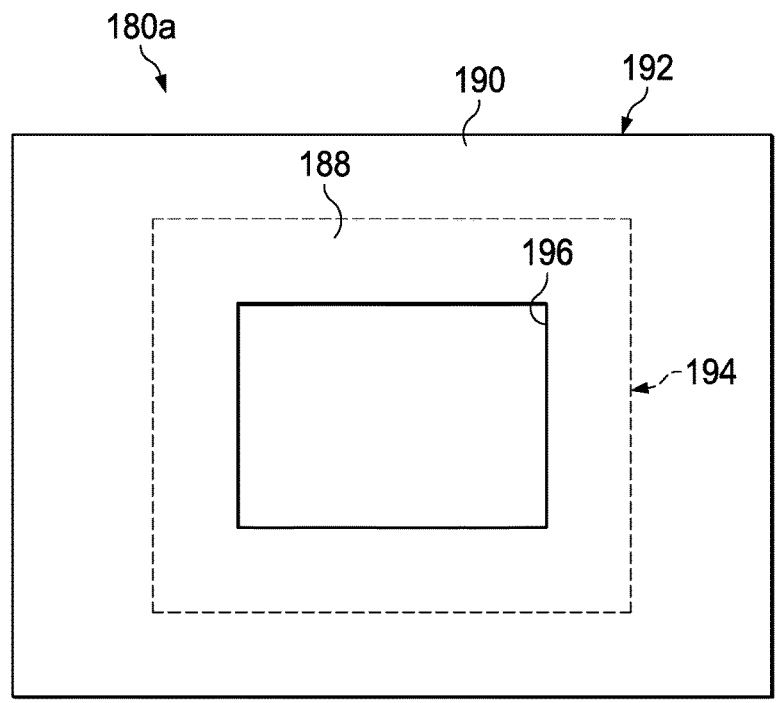
FIG. 7A is a plan view of an illustrative embodiment of an offloading layer suitable for use with the dressings, systems, and methods herein.
Figure 7B:
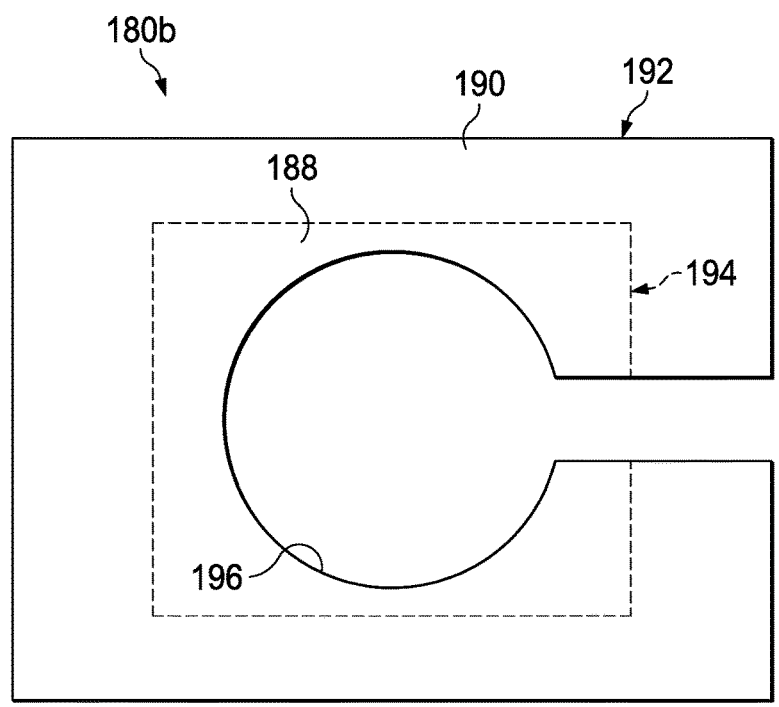
FIG. 7B is a plan view of another illustrative embodiment of an offloading layer suitable for use with the dressings, systems, and methods herein.
Figure 7C:
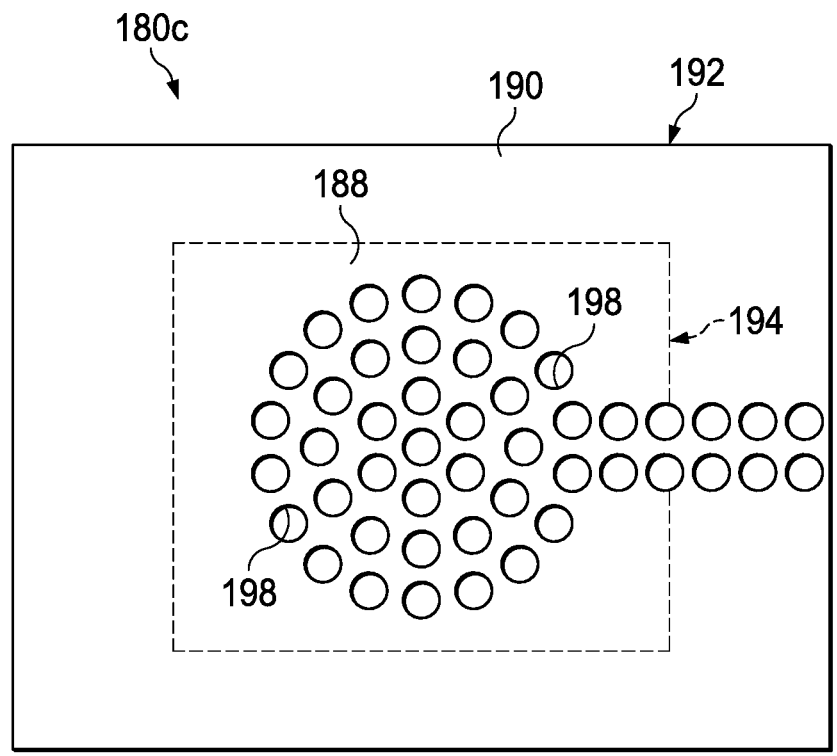
FIG. 7C is a plan view of yet another illustrative embodiment of an offloading layer suitable for use with the dressings, systems, and methods herein.

As shown in FIG. 6, in some embodiments, the offloading layer 180 may comprise a substantially continuous sheet. However, referring to FIGS. 7A-7C without limitation, other embodiments are also possible. For example, referring to FIG. 7A, in some embodiments, the offloading layer 180 may be an offloading layer 180*a* that may include an opening 196 in the force offloading region 188. Referring to FIG. 7B, in some embodiments, the offloading layer 180 may be an offloading layer 180*b* that may include the opening 196 in the force offloading region 188 and the target region 190 of the offloading layer 180*b*. Further, the opening 196 may extend from the force offloading region 188 to the target region 190 of the offloading layer 180*b* as shown in FIG. 7B. Referring to FIG. 7C, in some embodiments, the offloading layer 180 may be an offloading layer 180*c* that may include a plurality of perforations 198 disposed through the offloading layer 180*c* in the force offloading region 188. Although FIG. 7C also depicts the target region 190 of the offloading layer 180*c* as including the perforations 198, in other embodiments, the target region 190 of the offloading layer 180*c* may be substantially free of the perforations 198. A portion or portions of the offloading layer 180 may be removed to form the opening 196 in the offloading layer 180*a*, 180*b*, and the perforations 198 in the offloading layer 180*c*. The opening 196 and/or the perforations 198 among the embodiments of the offloading layer 180 may be shaped to accommodate the size or thickness of components of the system 102 and the dressing 124, such as, for example, the conduit interface 145 and the conduit 151 shown in FIG. 1. For example, portions of the offloading layer 180 including the opening 196 and/or the perforations 198 may provide a reduced thickness or density, and a reduced tendency to swell or expand during use, permitting components of the system 102 to be nested within of the offloading layer 180. Other shapes and configurations of the offloading layer 180 may be possible where such a reduction thickness or density of the offloading layer 180 may be beneficial.

Although the target region 190 among the embodiments of the offloading layer 180 may include the opening 196 and/or the perforations 198, the target region 190 may have a greater thickness, a greater density, or an increased tendency to swell or expand when in use relative to the force offloading region 188. For example, in some embodiments, the absorbent material of the offloading layer 180 may be positioned at least in the target region 190 of the offloading layer 180. In other embodiments, the target region 190 may have more of the absorbent material than the force offloading region 188. In yet other embodiments, the target region 190 may be more absorbent than the force offloading region 188.

Continuing with FIG. 6, the liquid deflector 178 may be positioned between the second side 186 of the fluid transport layer 176 and the offloading layer 180. In some embodiments, the liquid deflector 178 may be adapted to be positioned between the offloading layer 180 and the tissue site 104. The liquid deflector 178 may be configured to deflect liquid from the tissue site 104 into contact with the target region 190 of the offloading layer 180, and away from the force offloading region 188. Further, the liquid deflector 178 may be adapted to cover or be positioned adjacent to the force offloading region 188 of the offloading layer 180. The target region 190 of the offloading layer 180 may be adapted to be positioned around or at a periphery 200 of the liquid deflector 178.

The liquid deflector 178 may comprise a substantially liquid-impermeable material or film. In some embodiments, the liquid deflector 178 may comprise a thin and flexible polymer film. Materials suitable for the liquid deflector 178 may include, without limitation, polyurethane, thermoplastic elastomer, polythene, or polyester. The liquid deflector 178 may be held in place in the dressing 124 by, for example, adhesive, friction between the layers or components of the dressing 124, welding, or other medically accepted manner.

The target region 190 of the offloading layer 180 may be adapted to extend beyond the periphery 200 of the liquid deflector 178, leaving the target region 190 and the periphery 192 or edge of the offloading layer 180 exposed. For example, the liquid deflector 178 may have a surface area smaller than a surface area of the offloading layer 180. In some embodiments, the liquid deflector 178 may include a surface area between about 50 percent to about 80 percent of a surface area of the offloading layer 180. In this manner, liquid from the tissue site 104 may be directed around the periphery 200 of the liquid deflector 178 and into contact with the target region 190 and the periphery 192 or edge of the offloading layer 180.

Figure 8:
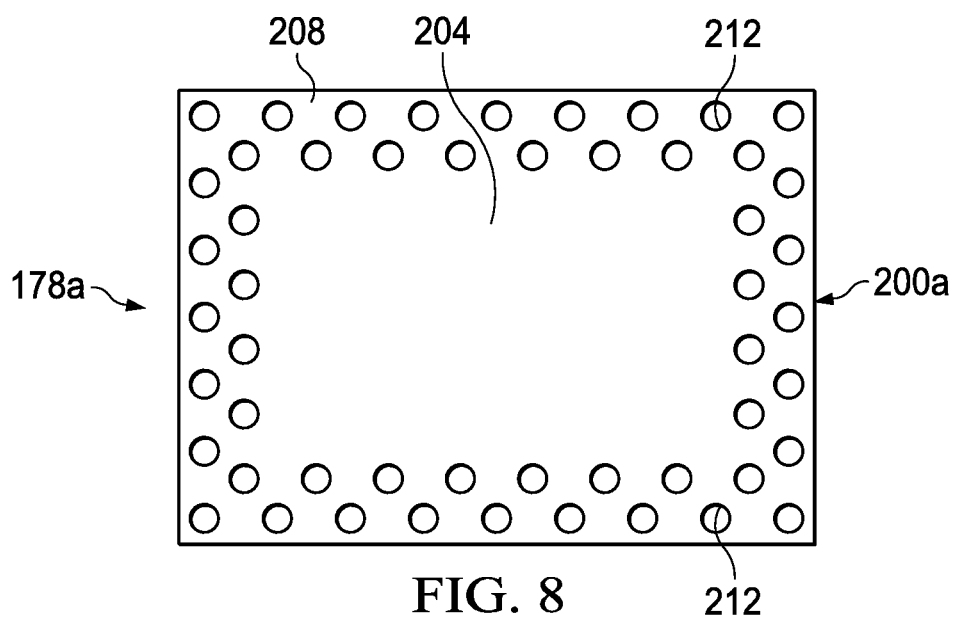
FIG. 8 is a plan view of an illustrative embodiment of a liquid deflector suitable for use with the dressings, systems, and methods herein.

In some embodiments, the liquid deflector 178 may comprise a substantially continuous sheet as shown in FIG. 6. However, referring to FIG. 8 without limitation, other embodiments are also possible. For example, as shown in FIG. 8, the liquid deflector 178 may be a liquid deflector 178a that may include a first portion 204 and a second portion 208. The second portion 208 may form an extended periphery 200a for the liquid deflector 178a. The first portion 204 may be adapted to cover or be positioned adjacent to the force offloading region 188 of the offloading layer 180, and the second portion 208 may be adapted to cover or be positioned adjacent to the target region 190 of the offloading layer 180. Thus, the periphery 200a of the liquid deflector 178a may be adapted to extend into the target region 190 of the offloading layer 180 proximate to the periphery 192 of the offloading layer 180. As shown in FIG. 8, the liquid deflector 178a may include an opening or a plurality of openings, such as a plurality of liquid deflector perforations 212, disposed through the second portion 208 of the liquid deflector 178a for providing fluid communication to the target region 190 of the offloading layer 180. The first portion 204 may be substantially free of the liquid deflector perforations 212. The liquid deflector perforations 212 may be variable in size and positioned to preferentially deflect liquid from the tissue site 104 into contact with the target region 190, or other desired region, of the offloading layer 180. Further, the liquid deflector perforations 212 may have any suitable shape.

Increasing the size or number of the liquid deflector perforations 212 may correspond to an increase in the amount of liquid from the tissue site 104 that may be brought into contact with the target region 190, or other desired region of the offloading layer 180, that is positioned adjacent to the liquid deflector perforations 212. Such an increase in the amount of liquid brought into contact with the offloading layer 180 may correspond to an increase in swelling or expansion of the particular region of the offloading layer 180 adjacent to the liquid deflector perforations 212. Thus, the liquid deflector perforations 212 may be positioned, sized, or configured according to the degree of swelling and expansion desired in a particular region of the offloading layer 180. Further, the liquid deflector perforations 212 may be omitted adjacent to regions of the offloading layer 180 where such swelling and expansion may not be desired.

The enclosing layer 182 may assist with positioning and retaining the offloading layer 180. For example, the enclosing layer 182 may be adapted to direct or orient the expansion or increase in thickness of the offloading layer 180 in a vertical direction, normal to the tissue site 104, while reducing or precluding lateral expansion of the offloading layer 180. In some embodiments, the enclosing layer 182 may be disposed or positioned between the sealing member 140 and the offloading layer 180. Further, in some embodiments, the enclosing layer 182 may be positioned between the fluid transport layer 176 and the sealing member 140. Further, in some embodiments, the periphery 187 of the fluid transport layer 176 may be coupled to a periphery 216 of the enclosing layer 182 to define an offloading enclosure 220, shown in FIGS. 9A-9B. The offloading enclosure 220 may be positioned around, surrounding, or encapsulating the offloading layer 180 between the fluid transport layer 176 and the enclosing layer 182.

The enclosing layer 182 may be comprised of similar materials configured to wick liquids in a lateral direction as described above for the fluid transport layer 176. In embodiments using reduced pressure, the use of such wicking materials for the enclosing layer 182 may also be suitable for use as a pressure distribution layer for distributing reduced pressure through the offloading layer 180 to the tissue site 104. However, in other embodiments, the enclosing layer 182 may comprise a porous mesh material or non-wicking material, which may be suitable for use without reduced pressure. The use of a non-wicking material for the enclosing layer 182 may prevent liquid from being redistributed over a side of the offloading layer 180 positioned opposite to the liquid deflector 178, which may beneficially cause clogging or gel-blocking in the offloading layer 180. Such clogging or gel-blocking may be desirable for slowing or preventing the wicking or migration of liquid from the tissue site 104 into the offloading region 188 from the target region 190 of the offloading layer 180. Suitable non-wicking materials for use in the enclosing layer 182 may include, without limitation, polyolefins, polyesters, polyamides, thermoplastic polyurethanes, thermoplastic elastomers, block co-polymers, PEBAX, acrylics, acetate co-polymers, or other such plastic materials.

Referring to FIGS. 9A-9B, FIG. 9A depicts the fluid management assembly 144 in an unsaturated state, and FIG. 9B depicts the fluid management assembly 144 in a saturated state during operation. During operation of the fluid management assembly 144, some liquid from the tissue site 104 may migrate from the target region 190 to the force offloading region 188. However, during operation, the force offloading region 188 may not be entirely saturated with the liquid, and the target region 190 may be expanded to a greater thickness than the force offloading region 188. Thus, when the tissue site 104 experiences a force, such as force 224 illustrated in FIG. 9B, the force 224 may be offloaded to the target region 190 and carried or supported by the target region 190 and the periphery 107 of the tissue site 104 when the target region 190 is positioned at the periphery 107 of the tissue site 104 as described herein. In some embodiments, about 6 millimeters to about 10 millimeters of clearance or difference in thickness or height maybe may be provided between the force offloading region 188 and the target region 190.

Figure 10:
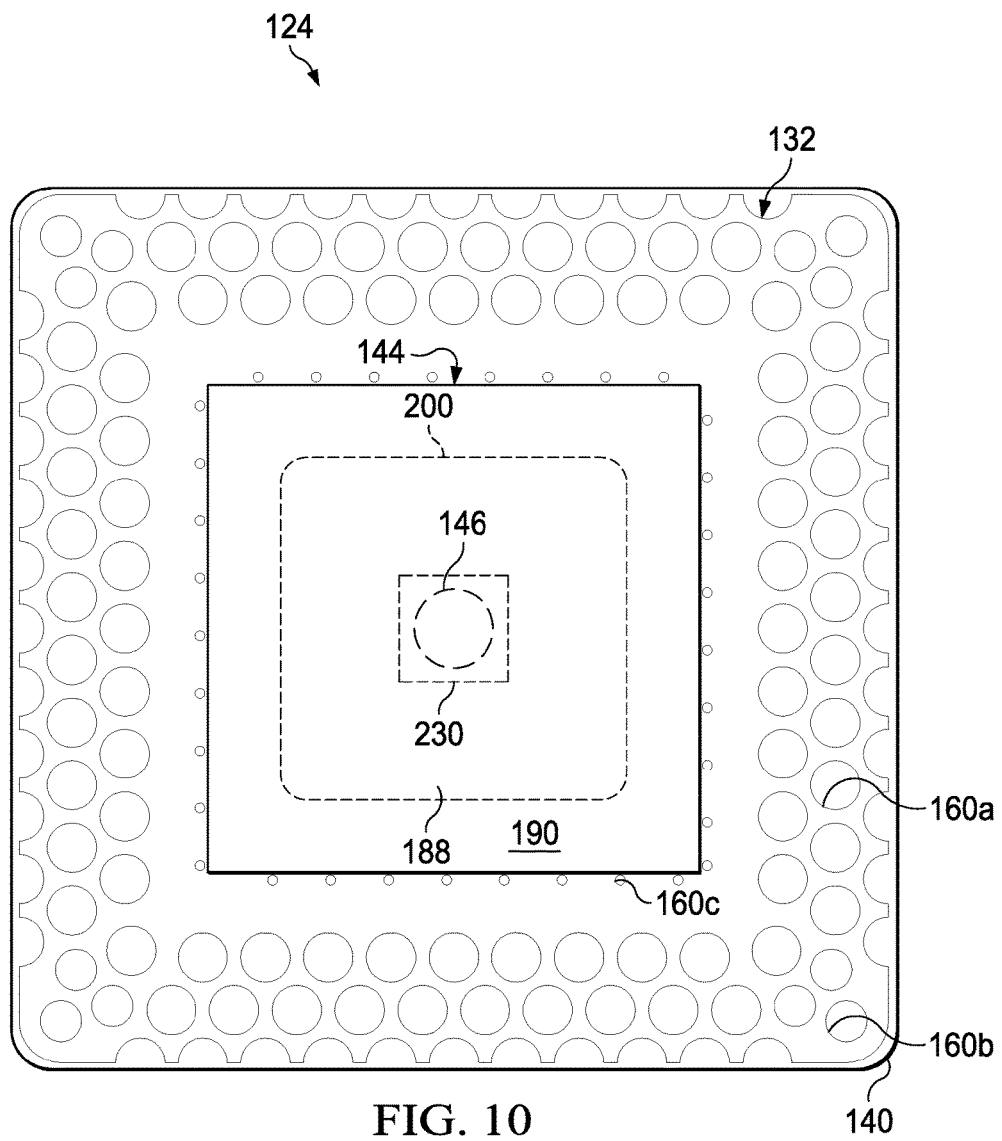
FIG. 10 is a plan view of an illustrative embodiment of a dressing, depicting illustrative embodiments of a force offloading region, a target region, and a dressing change indicator.

Referring to FIG. 10, in some embodiments, the dressing 124 may include a dressing guide indicator 230 visible on a side of the dressing 124 adapted to face away from the tissue site 104. The dressing guide indicator 230 may be substantially centered on the force offloading region 188 of the offloading layer 180. The dressing guide indicator 230 may be, for example, a printed circle or border to indicate when the dressing 124 may require removal or replacement due to excess liquid saturation of the force offloading region 188 from, for example, the migration or wicking of liquid from the target region 190. When the liquid reaches or contacts a perimeter or edge of the dressing guide indicator 230, removal or replacement of the dressing 124 may be recommended. Further, in some embodiments, the dressing 124 may comprise a color change dye (not shown) adapted to change color when in contact with liquid. The color change dye may be positioned substantially centered on the force offloading region 188 of the offloading layer 180 and visible on a side of the dressing 124 adapted to face away from the tissue site 104. Thus, a color change occurring in the color change dye may indicate that liquid has migrated sufficiently toward the center of the force offloading region 188 for removal or replacement of the dressing 124.

Figure 11:
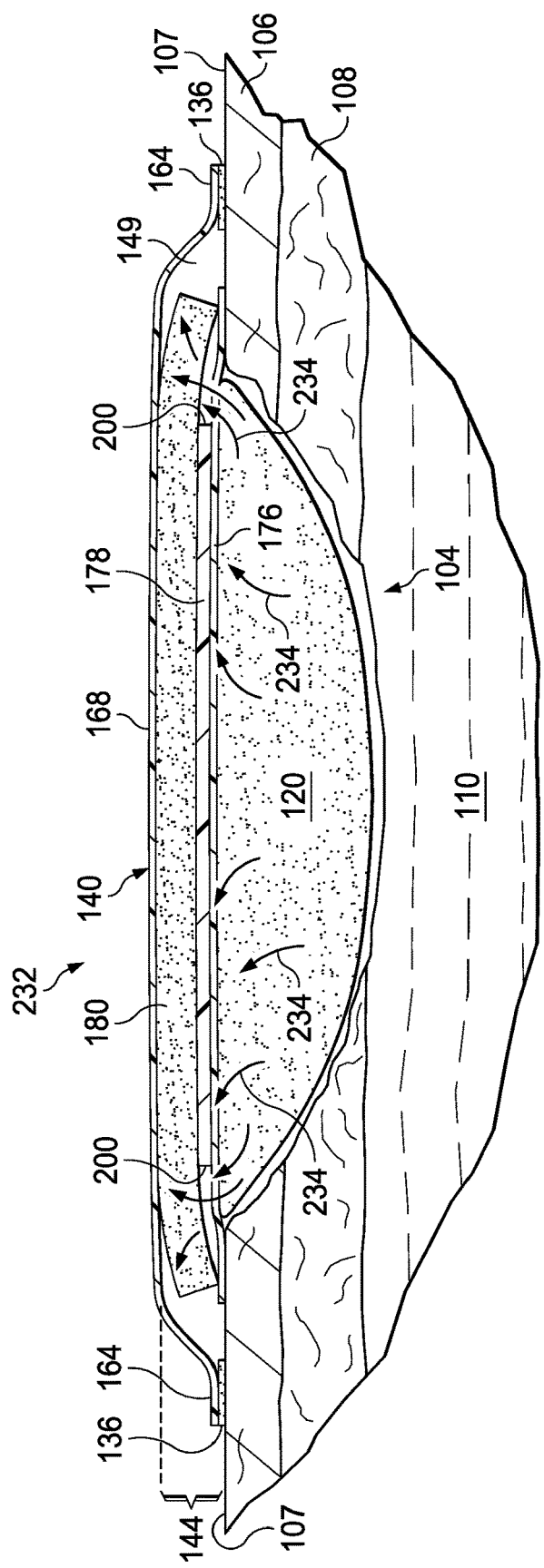
FIG. 11 is a cut-away view of another illustrative embodiment of a dressing for treating a tissue site.

Referring to FIG. 11, depicted is another illustrative embodiment of a dressing 232 suitable for use with the system 102 for treating the tissue site 104. Like reference characters shown among the figures may refer to like elements having similar structure and function as described above in connection with the dressing 124. Similar to the dressing 124 described above, the dressing 232 may include the fluid transport layer 176, the liquid deflector 178, and the offloading layer 180. Analogous to the dressing 124, the fluid transport layer 176, the liquid deflector 178, and the offloading layer 180 may provide the fluid management assembly 144 for the dressing 232. Further, the dressing 232 may include the optional interface manifold 120. However, as shown in FIG. 11, the base layer 132 and the enclosing layer 182 previously described for the dressing 124 may be omitted. In such an embodiment, the sealing member 140 may be directly adhered to tissue around or surrounding the tissue site 104, such as the epidermis 106. For example, the adhesive 136 may be positioned or applied between the periphery 164 of the sealing member 140 and the epidermis 106 to provide the sealed space 149. Further, FIG. 11 depicts fluid communication arrows 234 illustrating lateral wicking or movement of liquid from the tissue site 104 along the fluid transport layer 176, around the periphery 200 of the liquid deflector 178, and toward the offloading layer 180 according to some embodiments.

In operation of the system 102 according to some illustrative embodiments, the optional interface manifold 120 may be disposed against, proximate to, or in contact with the tissue site 104. The dressing 124, 232 may be applied over the optional interface manifold 120 and the tissue site 104 to form the sealed space 149. In some embodiments, the base layer 132 may be applied over, covering, or adjacent to the interface manifold 120 and tissue around or surrounding the tissue site 104. In other embodiments, the base layer 132 may be applied directly over, covering, or adjacent to the tissue site 104 and tissue around or surrounding the tissue site 104 without use of the optional interface manifold 120. In yet other embodiments, the base layer 132 may be omitted as described above for the dressing 232, and the sealing member 140 may be sealed about the tissue site 104 with the adhesive 136. Further, the force offloading region 188 of the offloading layer 180 in the dressing 124, 232 may be positioned substantially centered on, over, covering, or adjacent to the tissue site 104. The dressing guide indicator 230, being positioned substantially centered on or within the force offloading region 188 as described above, may assist the user with positioning the dressing 124, 232 at the tissue site 104.

In embodiments using the base layer 132, the materials described above for the base layer 132 may have a tackiness that may hold the dressing 124 initially in position. The tackiness may be such that if an adjustment is desired, the dressing 124 may be removed and reapplied. Once the dressing 124 is in the desired position, a force, such as hand pressure, may be applied on a side of the sealing member 140 opposite the tissue site 104 or facing away from the tissue site 104. The force applied to the sealing member 140 may cause at least some portion of the adhesive 136 to penetrate or extend through the plurality of apertures 160 and into contact with tissue around or surrounding the tissue site 104, such as the epidermis 106, to releaseably adhere the dressing 124 about the tissue site 104. In this manner, the configuration of the dressing 124 described above may provide an effective and reliable seal against challenging anatomical surfaces, such as an elbow or heal, at and around the tissue site 104. Further, the dressing 124 may permit re-application or re-positioning to, for example, correct air leaks caused by creases and other discontinuities in the dressing 124 and the tissue site 104. The ability to rectify leaks may increase the reliability of the therapy and reduce power consumption in some embodiments.

As the dressing 124, 232 comes into contact with liquid from the tissue site 104, the liquid may move toward the fluid management assembly 144. In embodiments using the base layer 132, the liquid may move through the apertures 160 in the base layer 132 before coming into contact with the fluid management assembly 144. The fluid management assembly 144 may wick or otherwise move the liquid through the optional interface manifold 120 and away from the tissue site 104. As described above, the interface manifold 120 may be adapted to communicate liquid from the tissue site 104 to the fluid management assembly 144, rather than store the liquid. Thus, in some embodiments, the fluid management assembly 144 may be more absorbent than the interface manifold 120. Configuring the fluid management assembly 144 to be more absorbent than the interface manifold 120 may provide an absorbent gradient through the dressing 124, 232 that may attract liquid from the tissue site 104 or the interface manifold 120 to the fluid management assembly 144. Thus, in some embodiments, the fluid management assembly 144 may be adapted to wick, pull, draw, or otherwise attract liquid from the tissue site 104 through the interface manifold 120. In the fluid management assembly 144, the liquid may initially come into contact with the fluid transport layer 176. The fluid transport layer 176 may distribute the liquid laterally along the surface of the fluid transport layer 176 as described above for contact with or absorption within the offloading layer 180.

As liquid from the tissue site 104 proceeds toward the offloading layer 180 of the dressing 124, 232, the liquid may be deflected or preferentially directed toward the target region 190 of the offloading layer 180 by the liquid deflector 178. When the liquid contacts the target region 190 of the offloading layer 180, the target region 190 may swell, expand, or otherwise increase in thickness from absorption of the liquid. The force offloading region 188 may be substantially free of contact with the liquid due to the deflection provided by the liquid deflector 178, and thus, the force offloading region 188 may be substantially or completely free of such swelling or expansion. However, the force offloading region 188 may exhibit some swelling or expansion as liquid from the tissue site 104 migrates through the offloading layer 180 from the target region 190 to the force offloading region 188. Although some expansion may occur in the force offloading region 188, the target region 190 of the offloading layer 180 may swell, expand, or otherwise increase in thickness more than the force offloading region 188. In this manner, the target region 190 may swell, expand, or otherwise increase in thickness around the periphery 107 of the tissue site 104, which can offload forces experienced at the tissue site 104 to tissue around or surrounding the tissue site 104. Accordingly, the dressing 124, 232 may provide physical pressure offloading at the tissue site 104 as a by-product of the liquid from the tissue site 104 being stored or otherwise managed within the dressing 124, 232. Removing or reducing this physical pressure, compressive force, or other force from the tissue site 104 may improve the healing of the tissue site 104.

Liquid pooling may occur in the target region 190 of the offloading layer 180 due to the deflection of liquid from the tissue site 104 to the target region 190. Such liquid pooling may cause gel-blocking, clogging, or other blockage within the offloading layer 180, which may preclude or otherwise slow the migration of the liquid through the offloading layer 180 from the target region 190 to the offloading region 188. In this manner, liquid from the tissue site 104 may preferentially be distributed around or circumferentially about the target region 190 and the periphery 107 of the tissue site 104, rather than to the force offloading region 188. However, after extended use of the dressing 124, 232, the liquid from the tissue site 104 may eventually wick or migrate from the target region 190 into contact with the force offloading region 188. Thus, some swelling, expansion, or increase in thickness may occur in the force offloading region 188 after extended use. If the liquid migrates sufficiently into the force offloading region 188 to cause localized swelling in the dressing 124, 232 over, covering, or adjacent to an area in which the offloading of force is desired, such as the tissue site 104, the dressing 124, 232 may require removal or replacement.

As described above, the dressing guide indicator 230 may be positioned substantially in the center of the force offloading region 188 for positioning the dressing 124, 232 over, covering, or adjacent to the tissue site 104 where the offloading of forces may be desired. Removal or replacement of the dressing 124, 232 may be recommended if the liquid from the tissue site 104 migrates through the offloading layer 180 proximate to or in contact with the dressing guide indicator 230 in the force offloading region 188. Accordingly, the dressing guide indicator 230 may indicate when the dressing 124, 232 requires removal or replacement in addition to assisting the user with initial placement of the dressing 124, 232 at the tissue site 104. Further, the color change dye referenced above may further alert the user when the dressing 124, 232 may need replacement by providing a color change when the liquid contacts or reacts with the color change dye.

Referring generally to the drawings, in some embodiments, a method of offloading a force at the tissue site 104 may include positioning the offloading layer 180 at the tissue site 104. The target region 190 of the offloading layer 180 may be positioned at the periphery 107 of the tissue site 104. Further, the method may include expanding at least the target region 190 of the offloading layer 180. In some embodiments, the target region 190 may be expanded more than the force offloading region 188. Further, in some embodiments, the offloading region 188 may be substantially free of expansion after expanding the target region 190 of the offloading layer 180.

In some embodiments, expanding at least the target region 190 of the offloading layer 180 may include increasing a thickness of at least the target region 190 of the offloading layer 180 in a direction normal to the tissue site 104. Further, in some embodiments, expanding at least the target region 190 of the offloading layer 180 may include deflecting liquid from the tissue site 104 into contact with the target region 190. Further, in some embodiments, expanding at least the target region 190 of the offloading layer 180 may include positioning the liquid deflector 178 between the tissue site 104 and the offloading layer 180.

In some embodiments, the method may include covering the force offloading region 188 of the offloading layer 180 with the liquid deflector 178. In some embodiments, the target region 190 of the offloading layer 180 may extend beyond the periphery 200 of the liquid deflector 178 such that liquid from the tissue site 104 is deflected around the periphery 200 of the liquid deflector 178 and into contact with the target region 190. Further, in some embodiments, the method may include covering the force offloading region 188 and the target region 190 of the offloading layer 180 with the liquid deflector 178, wherein the liquid deflector 178 includes the liquid deflector perforations 212 disposed through at least a portion of the liquid deflector 178 covering the target region 190.

In some embodiments, the method may include positioning the target region 190 of the offloading layer 180 at the periphery 200 of the liquid deflector 178. Further, in some embodiments, the method may include positioning the fluid transport layer 176 between the tissue site 104 and the liquid deflector 178; and wicking the liquid from the tissue site 104 along the fluid transport layer 176 in a lateral direction normal to a thickness of the fluid transport layer 176.

Although this specification describes advantages in the context of certain illustrative, non-limiting embodiments, various changes, substitutions, permutations, and alterations may be made without departing from the scope of the appended claims. Further, any feature described in connection with any one embodiment may also be applicable to any other embodiment.

We claim:

1. A system for treating a tissue site, comprising:
   a dressing, comprising:
      a base layer including a periphery, a central portion, and a plurality of apertures disposed through the base layer,
      a sealing member including a periphery and a central portion, the periphery of the sealing member coupled in contact with the periphery of the base layer,
      a fluid transport layer formed of a fibrous material and positioned between the base layer and the sealing member, the fluid transport layer comprising a hydrophilic side and a hydrophobic side, wherein the hydrophilic side is a fibrous surface configured to face the tissue site, an enclosing layer positioned between the fluid transport layer and the sealing member, an offloading layer positioned between the fluid transport layer and the enclosing layer, the offloading layer comprising a force offloading region and a target region, wherein a periphery of the fluid transport layer is coupled to a periphery of the enclosing layer surrounding the offloading layer between the fluid transport layer and the enclosing layer, and a liquid deflector positioned between the fluid transport layer and the offloading layer, the liquid deflector configured to deflect a liquid toward the target region of the offloading layer; and a reduced-pressure source adapted to be in fluid communication with the dressing to provide reduced pressure to the tissue site.

2. The system of claim 1, further comprising an adhesive configured to extend through the apertures at least in the periphery of the base layer and into contact with tissue around the tissue site.

3. The system of claim 1, wherein the central portion of the base layer is adapted to cover the tissue site and the periphery of the base layer is adapted to be positioned proximate to the tissue around the tissue site.

4. The system of claim 1, wherein the apertures in the base layer are adapted to be in fluid communication with the tissue site and the tissue around the tissue site, and wherein each of the apertures extends through opposing surfaces of the base layer to define an open area.

5. The system of claim 1, wherein the base layer is comprised of silicone.

6. The system of claim 1, further comprising an adhesive adapted to be in fluid communication with the tissue around the tissue site through the apertures in the base layer, and wherein the adhesive is positioned at least between the periphery of the sealing member and the periphery of the base layer.

7. The system of claim 1, wherein the sealing member is liquid impermeable and adapted to provide a sealed space between the sealing member and the tissue site.

8. The system of claim 1, wherein the fluid transport layer is adapted to wick the liquid from the tissue site along the fluid transport layer in a lateral direction normal to a thickness of the fluid transport layer.

9. The system of claim 1, wherein the target region of the offloading layer is adapted to expand in thickness upon contact with the liquid.

10. The system of claim 1, wherein the offloading layer comprises an absorbent material positioned at least in the target region.

11. The system of claim 1, wherein a portion of the offloading layer is removed in the force offloading region.

12. The system of claim 1, wherein the target region is positioned at a periphery of the force offloading region.

13. The system of claim 1, wherein the force offloading region is adapted to cover the tissue site, and wherein the target region is adapted to be positioned at a periphery of the tissue site.

14. The system of claim 1, wherein the liquid deflector comprises a substantially liquid-impermeable material.

15. The system of claim 1, wherein the liquid deflector is configured to deflect the liquid away from the force offloading region.

16. The system of claim 1, wherein the liquid deflector is adapted to be positioned between the offloading layer and the tissue site.

17. The system of claim 1, wherein the liquid deflector is adapted to cover the offloading region of the offloading layer, and wherein the target region of the offloading layer is adapted to be positioned at a periphery of the liquid deflector.

18. The system of claim 1, wherein the liquid deflector has a surface area smaller than a surface area of the offloading layer.

* * * * *